US009801859B2

(12) United States Patent
Toti et al.

(10) Patent No.: US 9,801,859 B2
(45) Date of Patent: Oct. 31, 2017

(54) BENDAMUSTINE FORMULATIONS

(71) Applicant: InnoPharma, Inc, Piscataway, NJ (US)

(72) Inventors: Udaya Toti, Monmouth Junction, NJ (US); Kumaresh Soppimath, Monmouth Jn, NJ (US); Rekha Nayak, Belle Mead, NJ (US); Satish Pejaver, Bridgewater, NJ (US); Navneet Puri, Bridgewater, NJ (US)

(73) Assignee: InnoPharma Licensing, LLC, Piscataway, NJ (US)

( * ) Notice: Subject to any disclaimer, the term of this patent is extended or adjusted under 35 U.S.C. 154(b) by 0 days.

(21) Appl. No.: 14/030,201

(22) Filed: Sep. 18, 2013

(65) Prior Publication Data

US 2014/0080880 A1    Mar. 20, 2014

Related U.S. Application Data

(60) Provisional application No. 61/702,673, filed on Sep. 18, 2012.

(51) Int. Cl.
| | | |
|---|---|---|
| *A61K 9/19* | (2006.01) | |
| *A61K 31/4184* | (2006.01) | |
| *A61K 9/00* | (2006.01) | |
| *A61K 47/26* | (2006.01) | |

(52) U.S. Cl.
CPC ........ *A61K 31/4184* (2013.01); *A61K 9/0019* (2013.01); *A61K 9/19* (2013.01); *A61K 47/26* (2013.01)

(58) Field of Classification Search
CPC ........ G06F 17/30725; G06K 19/06028; G06K 19/06037; G06K 7/10861; G07F 7/10; H04L 63/083; H04W 12/04; H04W 12/06; H04W 84/12; A61K 31/4184; A61K 47/26; A61K 9/0019; A61K 9/19
USPC ........................................................ 514/394
See application file for complete search history.

(56) References Cited

U.S. PATENT DOCUMENTS

| | | | | |
|---|---|---|---|---|
| 8,158,152 B2 * | 4/2012 | Palepu | ..................... | A61K 9/19 424/489 |
| 2006/0159713 A1 * | 7/2006 | Brittain et al. | ............... | 424/400 |
| 2009/0264488 A1 * | 10/2009 | Cooper et al. | ................ | 514/394 |
| 2011/0190363 A1 | 8/2011 | Drager et al. | | |

FOREIGN PATENT DOCUMENTS

| | | | |
|---|---|---|---|
| WO | WO 2012/103226 | * | 8/2012 |
| WO | 2013117969 | * | 8/2013 |

OTHER PUBLICATIONS

EC Safety Data Sheet, Ribomustin (Mar. 7, 1998, revised Jan. 3, 2007).*
CN 101966158, Feb. 9, 2011, English translation.*
Baheti et al. (J Excipients and Food Chem 1, 1, 2010, 41-54).*
Docagen (p. 1-9, 2010).*
Bedu-Addo (Pharmaceutical Technology, Lyophilization, 2004).*

* cited by examiner

*Primary Examiner* — Uma Ramachandran
(74) *Attorney, Agent, or Firm* — Jason G. Tebbutt

(57) ABSTRACT

A lyophilized bendamustine composition consisting of bendamustine hydrochloride, an aqueous solvent, and optionally an excipient, and a method of preparation thereof for treating a condition in a subject are provided. The aqueous solvent includes, for example, water, an acid, a base, or a salt, etc. The excipient includes at least one cryoprotectant, for example, sucrose, trehalose, mannitol, etc. A pre-lyophilization bendamustine composition is lyophilized, for example, by freezing, primary drying, annealing, secondary drying, condensed cooling and evacuation at preset temperatures to obtain the lyophilized bendamustine composition as a cake, a powder, or a solid concentrate. The lyophilized bendamustine composition is free of a non-aqueous solvent. Reconstitution is performed by mixing the lyophilized bendamustine composition with an aqueous solvent for about 30 seconds to 300 seconds. The reconstituted bendamustine product containing about 0.2 wt % to about 2.5 wt % by weight of impurities is administered to the subject in need thereof.

1 Claim, 14 Drawing Sheets

| INGREDIENTS | PRE-LYOPHILIZATION BENDAMUSTINE COMPOSITION I |
|---|---|
| BENDAMUSTINE HYDROCHLORIDE | 5 mg |
| MANNITOL | 8.5 mg |
| WATER FOR INJECTION | QUANTITY SUFFICIENT to 1.0 ml |

FIG. 3A

| STEP | PHASE | RAMP/HOLD | TEMPERATURE (°C) | TIME (min) | VACUUM (mTorr) |
|---|---|---|---|---|---|
|  | LOADING | N/A | <3 | N/A | N/A |
| 1 | FREEZING | RAMP | -48 | 365 | N/A |
| 2 | FREEZING | RAMP | -10 | 190 | N/A |
| 3 | FREEZING | HOLD | -10 | 180 | 100 |
| 4 | FREEZING | RAMP | -48 | 190 | 100 |
| 5 | FREEZING | HOLD | -48 | 180 | 100 |
| 6 | PRIMARY DRYING | RAMP | -20 | 140 | 100 |
| 7 | PRIMARY DRYING | HOLD | -20 | 480 | 100 |
| 8 | SECONDARY DRYING | RAMP | +20 | 200 | 100 |
| 9 | SECONDARY DRYING | HOLD | +20 | 360 | 100 |

FIG. 3B

| INGREDIENTS | PRE-LYOPHILIZATION BENDAMUSTINE COMPOSITION II |
|---|---|
| BENDAMUSTINE HYDROCHLORIDE | 5 mg |
| MANNITOL | 8.5 mg |
| WATER FOR INJECTION | QUANTITY SUFFICIENT TO 1.0 ml |

FIG. 4A

| STEP | PHASE | RAMP/HOLD | TEMPERATURE (°C) | TIME (min) | VACUUM (mTorr) |
|---|---|---|---|---|---|
|  | LOADING | N/A | <3 | N/A | N/A |
| 1 | FREEZING | RAMP | -48 | 365 | N/A |
| 2 | FREEZING | RAMP | -10 | 190 | N/A |
| 3 | FREEZING | HOLD | -10 | 180 | 100 |
| 4 | FREEZING | RAMP | -48 | 190 | 100 |
| 5 | FREEZING | HOLD | -48 | 180 | 100 |
| 6 | PRIMARY DRYING | RAMP | -20 | 140 | 100 |
| 7 | PRIMARY DRYING | HOLD | -20 | 480 | 100 |
| 8 | SECONDARY DRYING | RAMP | +25 | 200 | 100 |
| 9 | SECONDARY DRYING | HOLD | +25 | 360 | 100 |

FIG. 4B

| TESTS | LYOPHILIZED BENDAMUSTINE COMPOSITION I | LYOPHILIZED BENDAMUSTINE COMPOSITION II |
|---|---|---|
| 1. % IMPURITY | | |
| BENDAMUSTINE MONOHYDRATE | 0.25 | 0.30 |
| BENDAMUSTINE DIHYDRATE | BELOW DETECTION LIMIT | NONE DETECTED |
| 2. RECONSTITUTION TIME | 30 seconds to 60 seconds | 30 seconds to 60 seconds |

FIG. 5

| INGREDIENTS | PRE-LYOPHILIZATION BENDAMUSTINE COMPOSITION III |
|---|---|
| BENDAMUSTINE HYDROCHLORIDE | 5 mg |
| MANNITOL | 8.5 mg |
| WATER FOR INJECTION | QUANTITY SUFFICIENT TO 1.0 ml |

FIG. 6A

| STEP | PHASE | RAMP/HOLD | TEMPERATURE (°C) | TIME (min) | VACUUM (mTorr) |
|---|---|---|---|---|---|
|  | LOADING | N/A | <3 | N/A | N/A |
| 1 | FREEZING | RAMP | -48 | 100 | N/A |
| 2 | FREEZING | HOLD | -48 | 180 | N/A |
| 3 | ANNEALING | RAMP | -10 | 76 | N/A |
| 4 | ANNEALING | HOLD | -10 | 180 | N/A |
| 5 | FREEZING | RAMP | -48 | 76 | N/A |
| 6 | FREEZING | HOLD | -48 | 240 | N/A |
| 7 | PRIMARY DRYING | RAMP | -20 | 140 | 100 |
| 8 | PRIMARY DRYING | HOLD | -20 | 720 | 100 |
| 9 | SECONDARY DRYING | RAMP | +25 | 225 | 100 |
| 10 | SECONDARY DRYING | HOLD | +25 | 480 | 100 |

FIG. 6B

| TESTS | PRE-LYOPHILIZATION BENDAMUSTINE COMPOSITION III |
|---|---|
| 1. % IMPURITY | |
| BENDAMUSTINE MONOHYDRATE | 0.52 |
| BENDAMUSTINE DIHYDRATE | BELOW DETECTION LIMIT |
| 2. RECONSTITUTION TIME | 30 seconds to 90 seconds |

FIG. 6C

| INGREDIENTS | PRE-LYOPHILIZATION BENDAMUSTINE COMPOSITION IV |
|---|---|
| BENDAMUSTINE HYDROCHLORIDE | 5 mg |
| MANNITOL | 8.5 mg |
| WATER FOR INJECTION | QUANTITY SUFFICIENT TO 1.0 ml |

FIG. 7A

| STEP | PHASE | RAMP/HOLD | TEMPERATURE (°C) | TIME (min) | VACUUM (mTorr) |
|---|---|---|---|---|---|
|  | LOADING | N/A | <3 | N/A | N/A |
| 1 | FREEZING | RAMP | -48 | 100 | N/A |
| 2 | FREEZING | HOLD | -48 | 180 | N/A |
| 3 | ANNEALING | RAMP | -10 | 76 | N/A |
| 4 | ANNEALING | HOLD | -10 | 180 | N/A |
| 5 | FREEZING | RAMP | -48 | 76 | N/A |
| 6 | FREEZING | HOLD | -48 | 240 | 100 |
| 7 | PRIMARY DRYING | RAMP | -20 | 140 | 100 |
| 8 | PRIMARY DRYING | HOLD | -20 | 720 | 100 |
| 9 | SECONDARY DRYING | RAMP | +25 | 225 | 100 |
| 10 | SECONDARY DRYING | HOLD | +25 | 480 | 100 |

FIG. 7B

| TESTS | | INITIAL | 25±3°C/60±5%RH | | 40±3°C/75±5%RH | | |
|---|---|---|---|---|---|---|---|
| | | | 1M (INV) | 3M (INV) | 1M (INV) | 2M (INV) | 3M (INV) |
| APPEARANCE OF LYOPHILIZED CAKE | | WHITE LYOPHILIZED CAKE | WHITE LYOPHILIZED CAKE | WHITE LYOPHILIZED CAKE | WHITE LYOPHILIZED CAKE | WHITE LYOPHILIZED CAKE | WHITE LYOPHILIZED CAKE |
| RECONSTITUTION TIME | | 30-45 SECONDS | 30-60 SECONDS | 30-45 SECONDS | 30-60 SECONDS | 30-45 SECONDS | 30-45 SECONDS |
| IMPURITIES (%) | MONOHYDROXY-BENDAMUSTINE HYDROCHLORIDE | 0.49 | 0.47 | 0.57 | 0.45 | 0.52 | 0.55 |
| | DIHYDROXY-BENDAMUSTINE HYDROCHLORIDE | NOT DETECTED | NOT DETECTED | NOT DETECTED | NOT DETECTED | NOT DETECTED | NOT DETECTED |
| | UNKNOWN$_{(RRT)}$ | 0.06$_{(1.13)}$ | 0.08$_{(1.11)}$ | 0.08$_{(1.10)}$ | 0.08$_{(1.11)}$ | 0.07$_{(1.11)}$ | 0.05$_{(0.90)}$ 0.10$_{(1.10)}$ |
| | TOTAL (%) | 0.55 | 0.55 | 0.65 | 0.53 | 0.59 | 0.70 |

FIG. 7C

| INGREDIENTS | PRE-LYOPHILIZATION BENDAMUSTINE COMPOSITION V |
|---|---|
| BENDAMUSTINE HYDROCHLORIDE | 5 mg |
| MANNITOL | 8.5 mg |
| WATER FOR INJECTION | QUANTITY SUFFICIENT TO 1.0 ml |

FIG. 8A

| STEP | PHASE | RAMP/HOLD | TEMPERATURE (°C) | TIME (MIN) | VACUUM (mTorr) |
|---|---|---|---|---|---|
|  | LOADING | N/A | <3 | N/A | N/A |
| 1 | FREEZING | RAMP | -48 | 100 | N/A |
| 2 | FREEZING | HOLD | -48 | 180 | N/A |
| 3 | ANNEALING | RAMP | -10 | 76 | N/A |
| 4 | ANNEALING | HOLD | -10 | 180 | N/A |
| 5 | FREEZING | RAMP | -48 | 76 | N/A |
| 6 | FREEZING | HOLD | -48 | 240 | 100 |
| 7 | PRIMARY DRYING | RAMP | -20 | 140 | 100 |
| 8 | PRIMARY DRYING | HOLD | -20 | 720 | 100 |
| 9 | SECONDARY DRYING | RAMP | +25 | 225 | 100 |
| 10 | SECONDARY DRYING | HOLD | +25 | 480 | 100 |

FIG. 8B

| TESTS | | INITIAL | 25±3°C/60±5%RH | | 40±3°C/75±5%RH | | |
|---|---|---|---|---|---|---|---|
| | | | 1M (INV) | 3 M (INV) | 1 M (INV) | 2 M (INV) | 3 M (INV) |
| APPEARANCE OF LYOPHILIZED CAKE | | WHITE LYOPHILIZED CAKE | WHITE LYOPHILIZED CAKE | WHITE LYOPHILIZED CAKE | WHITE LYOPHILIZED CAKE | WHITE LYOPHILIZED CAKE | WHITE LYOPHILIZED CAKE |
| RECONSTITUTION TIME | | 90-120 SECONDS | 90-120 SECONDS | 90-120 SECONDS | 90-120 SECONDS | 90-120 SECONDS | 90-120 SECONDS |
| IMPURITIES (%) | MONOHYDROXY-BENDAMUSTINE HYDROCHLORIDE | 0.45 | 0.43 | 0.53 | 0.43 | 0.53 | 0.51 |
| | DIHYDROXY-BENDAMUSTINE HYDROCHLORIDE | NOT DETECTED | NOT DETECTED | NOT DETECTED | NOT DETECTED | NOT DETECTED | NOT DETECTED |
| | UNKNOWN$_{(RRT)}$ | 0.06$_{(1.13)}$ | 0.07$_{(1.13)}$ | 0.08$_{(1.10)}$ | 0.08$_{(1.13)}$ | 0.06$_{(1.11)}$ | 0.05$_{(0.90)}$ 0.08$_{(1.10)}$ |
| | TOTAL (%) | 0.51 | 0.57 | 0.62 | 0.60 | 0.59 | 0.65 |

FIG. 8C

| INGREDIENTS | PRE-LYOPHILIZATION BENDAMUSTINE COMPOSITION VI |
|---|---|
| BENDAMUSTINE HYDROCHLORIDE | 5 mg |
| MANNITOL | 8.5 mg |
| WATER FOR INJECTION | QUANTITY SUFFICIENT TO 1.0 ml |

FIG. 9A

| STEP | PHASE | RAMP/HOLD | TEMPERATURE (°C) | TIME (hours: minutes) | VACUUM (mTorr) |
|---|---|---|---|---|---|
|  | LOADING | N/A | 0 | 00:03 | N/A |
|  | FREEZING | HOLD | 0 | 00:10 |  |
| 1 | FREEZING | RAMP | -48 | 01:00 | N/A |
| 2 | FREEZING | HOLD | -48 | 03:00 | N/A |
| 3 | ANNEALING | RAMP | -10 | 01:10 | N/A |
| 4 | ANNEALING | HOLD | -10 | 03:00 | N/A |
| 5 | FREEZING | RAMP | -48 | 00:40 | N/A |
| 6 | FREEZING | HOLD | -48 | 04:00 | N/A |
| 7 | CONDENSER COOLING AND CHAMBER EVACUATION | N/A | NOT RECORDED | NOT RECORDED | NOT RECORDED |
| 8 | PRIMARY DRYING | RAMP | -20 | 02:20 | 100 |
| 9 | PRIMARY DRYING | HOLD | -20 | 24:00 | 100 |
| 10 | SECONDARY DRYING | RAMP | +25 | 04:15 | 100 |
| 11 | SECONDARY DRYING | HOLD | +25 | 24:00 | 100 |

FIG. 9B

| TEST PROCEDURE | | RESULTS | | | | | | |
|---|---|---|---|---|---|---|---|---|
| | | INITIAL | 4 WEEK | | 8 WEEK | 12 WEEK | | |
| | | | 25°C/60% RH | 40°C/75% RH | 40°C/75% RH | 25°C/60% RH INVERTED | 40°C/75% RH INVERTED |
| APPEARANCE | | WHITE LYOPHILIZED POWDER | WHITE LYOPHILIZED POWDER | WHITE LYOPHILIZED POWDER | WHITE LYOPHILIZED POWDER | WHITE LYOPHILIZED POWDER | WHITE LYOPHILIZED POWDER |
| RECONSTITUTION TIME | | <1 MIN | <1 MIN | <1 MIN | <1 MIN | <1 MIN | <1 MIN |
| APPEARANCE OF RECONSTITUTED SOLUTION | | SOLUTION FREE FROM VISIBLE PARTICLES OF FOREIGN MATTER | SOLUTION FREE FROM VISIBLE PARTICLES OF FOREIGN MATTER | SOLUTION FREE FROM VISIBLE PARTICLES OF FOREIGN MATTER | SOLUTION FREE FROM VISIBLE PARTICLES OF FOREIGN MATTER | SOLUTION FREE FROM VISIBLE PARTICLES OF FOREIGN MATTER | SOLUTION FREE FROM VISIBLE PARTICLES OF FOREIGN MATTER |
| % IMPURITIES | MONOHYDROXY-BENDAMUSTINE HYDROCHLORIDE | 0.78 | 0.81 | 0.68 | 0.66 | 0.74 | 0.69 |
| | DIHYDROXY-BENDAMUSTINE HYDROCHLORIDE | NOT DETECTED | NOT DETECTED | NOT DETECTED | NOT DETECTED | NOT DETECTED | NOT DETECTED |
| | HIGHEST UNKNOWN | 0.05% | <0.05% | <0.05% | <0.05% | <0.05% | 0.06% |
| | TOTAL | 0.83% | 0.81% | 0.73% | 0.66% | 0.74% | 0.80% |

FIG. 9C

| INGREDIENTS | PRE-LYOPHILIZATION BENDAMUSTINE COMPOSITION VII |
|---|---|
| BENDAMUSTINE HYDROCHLORIDE | 5 mg |
| MANNITOL | 8.5 mg |
| WATER FOR INJECTION | QUANTITY SUFFICIENT TO 1.0 ml |

FIG. 10A

| STEP | PHASE | RAMP/HOLD | TEMPERATURE (°C) | TIME (hours: minutes) | VACUUM (mTorr) |
|---|---|---|---|---|---|
| | LOADING | N/A | 0 | 00:03 | N/A |
| | FREEZING | HOLD | 0 | 00:10 | |
| 1 | FREEZING | RAMP | -48 | 00:56 | N/A |
| 2 | FREEZING | HOLD | -48 | 03:00 | N/A |
| 3 | ANNEALING | RAMP | -10 | 01:24 | N/A |
| 4 | ANNEALING | HOLD | -10 | 03:00 | N/A |
| 5 | FREEZING | RAMP | -48 | 00.43 | N/A |
| 6 | FREEZING | HOLD | -48 | 04:00 | N/A |
| 7 | CONDENSER COOLING AND CHAMBER EVACUATION | N/A | -48 | 01:31 | 100 |
| 8 | PRIMARY DRYING | RAMP | -20 | 02:42 | 100 |
| 9 | PRIMARY DRYING | HOLD | -20 | 25:00 | 100 |
| 10 | SECONDARY DRYING | RAMP | +25 | 04:13 | 100 |
| 11 | SECONDARY DRYING | HOLD | +25 | 43:42 | 100 |

FIG. 10B

| TEST PROCEDURE | | INITIAL | RESULTS | | | | | |
|---|---|---|---|---|---|---|---|---|
| | | | 4 WEEK | | 8 WEEK | 12 WEEK | | 12 WEEK* |
| | | | 25°C/60% RH | 40°C/75% RH | 40°C/75% RH | 25°C/60% RH INVERTED | 12 WEEKS 40°C/75% RH INVERTED |
| APPEARANCE | | WHITE LYOPHILIZED POWDER | WHITE LYOPHILIZED POWDER | WHITE LYOPHILIZED POWDER | WHITE LYOPHILIZED POWDER | WHITE LYOPHILIZED POWDER | WHITE LYOPHILIZED POWDER |
| RECONSTITUTION TIME | | <1 MINUTE | <1 MINUTE | <1 MINUTE | <1 MINUTE | <1 MINUTE | <1 MINUTE |
| APPEARANCE OF RECONSTITUTED SOLUTION | | SOLUTION FREE FROM VISIBLE PARTICLES OF FOREIGN MATTER | SOLUTION FREE FROM VISIBLE PARTICLES OF FOREIGN MATTER | SOLUTION FREE FROM VISIBLE PARTICLES OF FOREIGN MATTER | SOLUTION FREE FROM VISIBLE PARTICLES OF FOREIGN MATTER | SOLUTION FREE FROM VISIBLE PARTICLES OF FOREIGN MATTER | SOLUTION FREE FROM VISIBLE PARTICLES OF FOREIGN MATTER |
| % IMPURITIES | MONOHYDROXY-BENDAMUSTINE HYDROCHLORIDE | 0.84 | 0.83 | 0.94 | 0.93 | 0.92 | 0.87 |
| | DIHYDROXY-BENDAMUSTINE HYDROCHLORIDE | NOT DETECTED | NOT DETECTED | NOT DETECTED | NOT DETECTED | NOT DETECTED | NOT DETECTED |
| | HIGHEST UNKNOWN | <LOQ | <0.05 | <0.05 | <0.05 | <0.05 | 0.09 |
| | TOTAL | 0.84 | 0.83 | 0.99 | 0.93 | 0.92 | 0.96 |

FIG. 10C

BENDAMUSTINE FORMULATIONS

CROSS REFERENCE TO RELATED APPLICATIONS

This application claims the benefit of provisional patent application No. 61/702,673 titled "Formulation Of Bendamustine Formulations", filed in the United States Patent and Trademark Office on Sep. 18, 2012.

The specification of the above referenced patent application is incorporated herein by reference in its entirety.

BACKGROUND

The compositions disclosed herein, in general, relate to pharmaceutical compositions containing a bifunctional alkylating agent. More particularly, the compositions disclosed herein relate to stable, pharmaceutically acceptable compositions prepared from bendamustine. Furthermore, the method disclosed herein relates to preparation of such compositions for treating a condition in a subject in need thereof.

Bendamustine is a drug that was first synthesized in the 1960s with high potency in the treatment of several tumoral diseases and has been in clinical use since 1985. Bendamustine functions as a bifunctional alkylating agent with antimetabolic and cytotoxic activity indicated for treatment of subjects with chronic lymphocytic leukemia (CLL) and indolent B-cell non-Hodgkin's lymphoma (NHL) that has progressed during or within six months of treatment with rituximab or a rituximab containing regimen. Efficacy relative to first line therapies other than a chlorambucil drug used in the treatment of CLL has not been established. A molecule of bendamustine comprises three structural elements, namely, a mechlorethanamine group, a benzimidazole core, and a butyric acid chain. The butyric acid chain together with a protonated heterocycle mediates water solubility. The benzimidazole moiety should lead to tumor cell accumulation by purine base transporters.

Bendamustine was developed in the 1960s by East German pharmacologists with an aim of combining a 2-chloroethylamine group of nitrogen mustard derivatives with a benzimidazole ring system of purine analogues. Bendamustine entered clinical trial in 1969 to treat multiple myeloma (MM) and entered the German market in the early 1970s. Bendamustine was marketed in Germany from 1971 to 1992 as Cytostasan and from 1993 to present as Ribomustin. Because of the high reactivity of bendamustine in aqueous solutions, nitrogen mustards are difficult to formulate as pharmaceuticals and are often supplied for administration in a lyophilized form. The lyophilized form of bendamustine requires reconstitution, typically in water, by skilled medical personnel prior to administration. Once in an aqueous solution, nitrogen mustards are subject to degradation by hydrolysis and therefore the reconstituted product should be administered to a subject as soon as possible after reconstitution.

Reconstitution of a powdered lyophilized bendamustine product such as Ribomustin using existing reconstitution techniques is difficult. Typically, the reconstitution time for the lyophilized bendamustine product varies from about fifteen minutes to about thirty minutes. The level of impurities in the lyophilized bendamustine product manufactured using water and various solvent mixtures is about 0.9 wt % after reconstitution. Porous lyophilized bendamustine generated using a solvent and a water mixture has a lesser reconstitution time of about 3 minutes to about 10 minutes as compared to the commercially available Ribomustin which takes about fifteen minutes to about thirty minutes to reconstitute. However, a reconstitution time of even 3 minutes to 10 minutes generates high impurity levels in the lyophilized bendamustine product. Moreover, as manufacture of the lyophilized bendamustine product involves organic solvents, making the final product free from solvents is difficult. Furthermore, environmental and safety implications are difficult to control during commercial manufacture of the bendamustine product. In 2005, after formal clinical development programs were conducted in the USA and in Europe, the bendamustine product was made available for use in the USA and United Kingdom (UK) under the trade names Treanda® by Cephalon, Inc., and Levact® by Mundipharma AG, respectively. However, many of the issues mentioned above still remain with these products.

The drug Treanda® is intended for intravenous infusion into subjects suffering from tumoral diseases only after reconstitution with sterile water for injection in United States Pharmacopeia (USP) unit, and after further dilution with either 0.9 wt % sodium chloride injection in USP unit, or 2.5 wt % dextrose/0.45 wt % sodium chloride injection in USP unit. The drug Treanda® is supplied as a sterile non-pyrogenic white to off-white lyophilized powder in a single use vial. Each 25 mg vial contains 25 mg of bendamustine hydrochloride and 42.5 mg of mannitol in USP unit. Each 100 mg vial comprises 100 mg of bendamustine hydrochloride and 170 mg of mannitol in USP unit. The pH of the reconstituted solution is 2.5 to 3.5. As per the package insert of the drug Treanda®, the vial comprising the drug Treanda® should be aseptically reconstituted as follows: for a 25 mg vial comprising the drug Treanda®, 5 mL of only sterile water is added for injection in USP unit; for a 100 mg vial comprising the drug Treanda®, 20 mL of only sterile water is added for injection in USP unit. The vial should then be shaken well to yield a clear, colorless to a pale yellow solution with a bendamustine hydrochloride concentration of 5 mg/mL. As per the package insert, the lyophilized product should completely dissolve in 5 minutes. Though the drug Treanda® has shown a relatively smaller reconstitution time compared to its predecessor, 5 minutes is still a significant time for reconstitution which can generate higher impurities considering the instability of the drug Treanda®.

Hence, there is a long felt but unresolved need for lyophilized formulations of bendamustine hydrochloride that do not use non-aqueous solvents as part of the bendamustine hydrochloride composition or its formulation process. Moreover, there is a need for a method for preparing a stable lyophilized bendamustine hydrochloride composition that reconstitutes easily, yields a better impurity profile than the existing bendamustine product, takes a shorter time to administer to a subject in need thereof than bendamustine hydrochloride products in the market, and makes the composition more physician or nurse friendly.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

Disclosed herein is a bendamustine hydrochloride pharmaceutical composition, herein a "bendamustine composition", and a method for preparation thereof for treating a condition, for example, cancer in a subject, for example, a human or an animal. Also, the term "bendamustine hydrochloride" will herein be referred to as "bendamustine". The bendamustine composition disclosed herein addresses the above stated need for a lyophilized formulation of bendamustine that does not use non-aqueous solvents as part of the bendamustine composition or formulation process, and uses only aqueous solvents as a constituent of the bendamustine composition and as part of the formulation process. The method disclosed herein addresses the above stated need for preparing a lyophilized bendamustine composition with an aqueous solvent that reconstitutes easily, yields a better impurity profile than an existing bendamustine product, and makes the bendamustine composition easier to administer and more physician or nurse friendly. The bendamustine composition disclosed herein and method of preparation thereof provides bendamustine hydrochloride in an aqueous solvent at low temperatures followed by a lyophilization cycle to produce a lyophilized bendamustine product with an acceptable degradation profile and low reconstitution time. As used herein, the term "reconstitution time" refers to the time required to rehydrate and dissolve the lyophilized bendamustine product in an aqueous solvent or a diluent. Herein, all constituents are entered as percent by weight based on the total weight of the composition of which they form a part.

Disclosed herein is a method for preparing a lyophilized bendamustine composition for treating a condition in a subject in need thereof. The method disclosed herein comprises preparing a pre-lyophilization bendamustine composition consisting of bendamustine hydrochloride, an aqueous solvent, and optionally an excipient. The bendamustine hydrochloride is present at a concentration of, for example, about 0.01 wt % to about 90 wt % by weight of the pre-lyophilization bendamustine composition. The bendamustine hydrochloride functions as a bifunctional alkylating agent. The aqueous solvent is present at a concentration of, for example, about 30 wt % to about 99.9 wt % by weight of the pre-lyophilization bendamustine composition. In an embodiment, the aqueous solvent comprises at least one of: about 30 wt % to about 99.5 wt % by weight of water, about 5 wt % to about 20 wt % by weight of an aqueous buffer, about 5 wt % to about 20 wt % by weight of saline, about 0.01 wt % to about 50 wt % by weight of at least one cryoprotectant, about 0.01 wt % to about 50 wt % by weight of at least one aqueous soluble excipient, or any combination thereof based on the weight of the pre-lyophilization bendamustine composition. The cryoprotectant comprises, for example, at least one of sucrose, trehalose, lactose, mannitol, sorbitol, colloidal silicon dioxide, maltose, polyvinylpyrrolidone, fructose, dextran, glycerol, polyvinyl alcohol, glycine, hydroxypropyl-β-cyclodextrin, gelatin, histidine, glycine, and any combination thereof. In an embodiment, the aqueous solvent in the pre-lyophilization bendamustine composition consists predominantly of water, for example, about 30 wt % to about 99.9 wt % by weight of the pre-lyophilization bendamustine composition.

In an embodiment, an excipient is optionally present in the pre-lyophilization bendamustine composition at a concentration of, for example, about 0.01 wt % to about 50 wt % by weight of the pre-lyophilization bendamustine composition. The excipient comprises, for example, one of antioxidants, preservatives, stabilizers, mixtures, bulking agents, buffers, isotonicity agents, etc., and any combination thereof. The antioxidants comprise, for example, butylated hydroxytoluene, butylated hydroxyanisole, propyl gallate, α-tocopherol, tocopherol polyethylene glycol succinate, L-cysteine, sodium ethylenediaminetetraacetic acid, thioglycerol, etc., and any combination thereof. In an embodiment, the buffers comprise, for example, citric acid, acetic acid, maleic acid, phosphoric acid, succinic acid, tartaric acid, counter ion salts, etc., and any combination thereof. The pre-lyophilization bendamustine composition has a pH between 1 and 14. The pre-lyophilization bendamustine composition is free of a non-aqueous solvent.

In an embodiment, the pre-lyophilization bendamustine composition is packaged in one or more containers, for example, vials, ampoules, etc., and other pharmaceutically acceptable containers. The pre-lyophilization bendamustine composition is prepared at a preset temperature between about −5° C. and about 15° C. For example, in an embodiment, the pre-lyophilization bendamustine composition is prepared at a preset temperature of about 3° C. As an example, the prepared pre-lyophilization bendamustine composition consists of about 0.5 wt % by weight of bendamustine hydrochloride, about 98.65 wt % by weight of an aqueous solvent, and about 0.85 wt % by weight of an excipient.

After preparation of the pre-lyophilization bendamustine composition, the prepared pre-lyophilization bendamustine composition is lyophilized to obtain the lyophilized bendamustine composition. In an embodiment, the prepared bendamustine composition is lyophilized by freezing the prepared pre-lyophilization bendamustine composition at a preset temperature between about −20° C. and about −50° C. For example, in an embodiment, the prepared pre-lyophilization bendamustine composition is lyophilized by freezing the prepared pre-lyophilization bendamustine composition at a preset temperature of about −48° C. In another embodiment, the prepared pre-lyophilization bendamustine composition is lyophilized by primary drying the prepared pre-lyophilization bendamustine composition at a preset temperature between about −10° C. and about −35° C. For example, in an embodiment, the prepared pre-lyophilization bendamustine composition is lyophilized by primary drying the prepared pre-lyophilization bendamustine composition at a preset temperature of about −15° C. The primary drying of the prepared pre-lyophilization bendamustine composition is carried out at a preset pressure, for example, between about 50 millitorr (mTorr) and about 150 mTorr. For example, in an embodiment, the primary drying of the prepared pre-lyophilization bendamustine composition is carried out at a preset pressure of about 100 mTorr.

In an embodiment, the lyophilization of the prepared pre-lyophilization bendamustine composition comprises annealing of the prepared pre-lyophilization bendamustine composition at a preset temperature between about −60° C. and about −5° C. For example, the prepared pre-lyophilization bendamustine composition is lyophilized by annealing the prepared pre-lyophilization bendamustine composition at a preset temperature from about −48° C. to about −10° C. The annealing of the prepared pre-lyophilization bendamustine composition is performed prior to and/or after freezing the prepared pre-lyophilization bendamustine composition. In another embodiment, the lyophilization of the prepared pre-lyophilization bendamustine composition comprises secondary drying of the prepared pre-lyophilization bendamustine composition at a preset temperature, for example, between about 15° C. and about 30° C. For example, in an embodiment, the prepared pre-lyophilization bendamustine composition is lyophilized by secondary drying the prepared pre-lyophilization bendamustine composition at a preset temperature of about 20° C.

The secondary drying of the prepared pre-lyophilization bendamustine composition is carried out at a preset pressure, for example, between about 50 mTorr and about 150 mTorr. For example, the secondary drying of the prepared pre-lyophilization bendamustine composition is carried out at a preset pressure of about 100 mTorr. In an embodiment, the lyophilization of the prepared pre-lyophilization bendamustine composition comprises condensed cooling and evacuation of the prepared pre-lyophilization bendamustine composition at a temperature of, for example, about −48° C. prior to the primary drying of the prepared pre-lyophilization bendamustine composition. The prepared pre-lyophilization bendamustine composition is lyophilized, for example, into a cake, a powder, a solid concentrate, etc. The lyophilized bendamustine composition, after lyophilization, comprises about 0.2 wt % to about 2.5 wt % of any specified or unspecified impurity by weight of the lyophilized bendamustine composition.

The lyophilized bendamustine composition consists of bendamustine hydrochloride, an aqueous solvent, and optionally an excipient. The bendamustine hydrochloride is present in the lyophilized bendamustine composition at a concentration of, for example, about 1 wt % to about 99 wt % by weight of the lyophilized bendamustine composition. The aqueous solvent is present in the lyophilized bendamustine composition at a concentration of, for example, about 0.01 wt % to about 5 wt % by weight of the lyophilized bendamustine composition. In an embodiment, the aqueous solvent comprises, for example, about 30 wt % to about 99.9 wt % of water by weight of the lyophilized bendamustine composition. The aqueous solvent comprises at least one of an acid, a base, a salt, and about 1 wt % to about 99 wt % of at least one aqueous soluble excipient by weight of the lyophilized bendamustine composition. The excipient is present in the lyophilized bendamustine composition at a concentration of, for example, about 1 wt % to about 99 wt % by weight of the lyophilized bendamustine composition. The excipient comprises, for example, about 0.01 wt % to about 65 wt % of at least one cryoprotectant by weight of the lyophilized bendamustine composition. The lyophilized bendamustine composition is free of a non-aqueous solvent.

The degradation, that is, the total impurities of the lyophilized bendamustine product is about 0.80 wt % to about 0.96 wt % when the lyophilized bendamustine product is stored for 3 months at 40° C. and 75% relative humidity (RH). The degradation of the lyophilized bendamustine product is about 0.74 wt % to about 0.92 wt % when the lyophilized bendamustine product is stored for 3 months at 25° C. and 60% RH. The degradation of the lyophilized bendamustine product is about 1.0 wt % to about 1.2 wt % when the lyophilized bendamustine product is stored for 6 months at 40° C. and 75% RH. The degradation of the lyophilized bendamustine product is about 0.89 wt % to about 1.1 wt % when the lyophilized bendamustine product is stored for 6 months at 25° C. and 60% RH.

The lyophilized bendamustine composition is reconstituted with an aqueous solvent by mixing the lyophilized bendamustine product with the aqueous solvent, for example, for about 30 seconds to about 300 seconds. The aqueous solvent used for the reconstitution of the lyophilized bendamustine composition is a pharmaceutically acceptable solvent, for example, water for injection, etc. In an embodiment, the lyophilized bendamustine composition is reconstituted in about 30 seconds to about 60 seconds. The bendamustine hydrochloride is present in the reconstituted bendamustine product at a concentration of about 0.01 wt % to about 90 wt % by weight of the reconstituted bendamustine product. The aqueous solvent is present in the reconstituted bendamustine product at a concentration of about 30 wt % to about 99.9 wt % by weight of the reconstituted bendamustine product. The excipient is present in the reconstituted bendamustine product at a concentration of about 0.01 wt % to about 50 wt % by weight of the reconstituted bendamustine product. As an example, the reconstituted bendamustine product contains about 0.5% bendamustine hydrochloride, 0.85% mannitol, and about 98.65% water for injection. The reconstituted bendamustine product comprises, for example, about 0.2 wt % to about 2.5 wt % by weight of specified impurities and/or unspecified impurities.

The steps listed below are performed under aseptic conditions to reconstitute the lyophilized bendamustine composition. About 30 wt % to about 99.9 wt % of an aqueous solvent is mixed with about 0.01 wt % to about 50 wt % of an excipient based on the total weight of the pre-lyophilization bendamustine composition in a first compounding vessel at a preset temperature, for example, between about −2° C. and about 15° C., until the excipient dissolves in the aqueous solvent. The aqueous solvent-excipient mixture in the first compounding vessel is maintained at a preset temperature between about −2° C. and about 15° C. About 0.01 wt % to about 90 wt % of bendamustine hydrochloride based on the total weight of the pre-lyophilization bendamustine composition is mixed with about 5 wt % of a chilled aqueous solvent in a second compounding vessel until a uniform slurry is formed. The uniform slurry is then added to the first compounding vessel containing the aqueous solvent-excipient mixture maintained at the preset temperature between about −2° C. and about 15° C. The contents of the first compounding vessel are mixed until the contents dissolve completely. The contents of the first compounding vessel are then adjusted to a final weight using an aqueous solvent chilled at a preset temperature between about −2° C. and about 15° C. In an embodiment, the preset temperature is maintained at about −2° C. to about 3° C. in the above steps. The adjusted contents in the first compounding vessel are filtered, for example, through a 0.22 micron filter membrane to obtain the reconstituted bendamustine product.

In an embodiment, the lyophilized bendamustine composition is reconstituted as follows: In a pharmaceutically acceptable container, for example, a vial containing the lyophilized bendamustine composition, a diluent, for example, water for injection, 0.9% sodium chloride, 2.5% dextrose/0.45% sodium chloride, etc., is injected in a quantity sufficient to obtain the desired bendamustine concentration. The contents of the container are swirled until the lyophilized bendamustine composition dissolves, leaving no visible residue as undissolved matter, and the solution is not significantly less clear than the diluent, and essentially free from visible particles. In an embodiment, the reconstitution time of the lyophilized bendamustine composition in accordance with this procedure is, for example, about 30 seconds to about 60 seconds. The reconstituted bendamustine product in the container is then transferred to an infusion bag for preparation of the ready to administer bendamustine product as recited below.

The reconstituted bendamustine product is transferred to an infusion bag at room temperature, for example, at about 15° C. to about 30° C. within 30 minutes after the bendamustine product is reconstituted. The reconstituted bendamustine product is diluted with a diluent, for example, 0.9% sodium chloride injection, 2.5% dextrose/0.45% sodium chloride injection, etc., to obtain a ready to administer, bendamustine solution which is stable for 24 hours when stored at about 2° C. to about 8° C., or stable for 3 hours when stored at room temperature, for example, at about 15°

C. to about 30° C. under room lighting. Administration of the ready to administer bendamustine solution to a subject in need thereof must be completed within the above referenced 24 hour or 3 hour period.

The bendamustine hydrochloride is present in the ready to administer bendamustine product at a concentration of about 0.01 wt % to about 1 wt % by weight of the ready to administer bendamustine product with the balance of the composition consisting of an aqueous solvent and optionally an excipient. In an embodiment, bendamustine hydrochloride is present in the ready to administer bendamustine product at a concentration of about 0.02 wt % to about 0.06 wt % by weight of the ready to administer bendamustine product with the balance of the composition consisting of an aqueous solvent and optionally an excipient. The aqueous solvent is present in the ready to administer bendamustine product at a concentration of about 99 wt % to about 99.95 wt % by weight of the ready to administer bendamustine product. The excipient is present in the ready to administer bendamustine product at a concentration of about 0.034 wt % to about 0.102 wt % by weight of the ready to administer bendamustine product.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and components disclosed herein.

FIG. 3A exemplarily illustrates a table showing a pre-lyophilization bendamustine composition I.

FIG. 3B exemplarily illustrates a table showing a method for lyophilizing the pre-lyophilization bendamustine composition I shown in FIG. 3A.

FIG. 4A exemplarily illustrates a table showing a pre-lyophilization bendamustine composition II.

FIG. 4B exemplarily illustrates a table showing a method for lyophilizing the pre-lyophilization bendamustine composition II shown in FIG. 4A.

FIG. 5 exemplarily illustrates a table showing impurities generated during lyophilization of the pre-lyophilization bendamustine compositions I and II shown in FIG. 3A and FIG. 4A respectively, based on the steps of the methods shown in FIG. 3B and FIG. 4B respectively, and the reconstitution times of the corresponding lyophilized bendamustine compositions I and II respectively.

FIG. 6A exemplarily illustrates a table showing a pre-lyophilization bendamustine composition III.

FIG. 6B exemplarily illustrates a table showing a method for lyophilizing the pre-lyophilization bendamustine composition III shown in FIG. 6A.

FIG. 6C exemplarily illustrates a table showing impurities generated during lyophilization of the pre-lyophilization bendamustine composition III shown in FIG. 6A based on the steps of the method shown in FIG. 6B, and the reconstitution times of the lyophilized bendamustine composition.

FIG. 7A exemplarily illustrates a table showing a pre-lyophilization bendamustine composition IV.

FIG. 7B exemplarily illustrates a table showing a method for lyophilizing the pre-lyophilization bendamustine composition IV shown in FIG. 7A.

FIG. 7C exemplarily illustrates a table showing impurities generated during lyophilization of the pre-lyophilization bendamustine composition IV shown in FIG. 7A based on the steps of the method shown in FIG. 7B, and the reconstitution times of the lyophilized bendamustine composition.

FIG. 8A exemplarily illustrates a table showing a pre-lyophilization bendamustine composition V.

FIG. 8B exemplarily illustrates a table showing a method for lyophilizing the pre-lyophilization bendamustine composition V shown in FIG. 8A.

FIG. 8C exemplarily illustrates a table showing impurities generated during lyophilization of the pre-lyophilization bendamustine composition V shown in FIG. 8A based on the steps of the method shown in FIG. 8B, and the reconstitution times of the lyophilized bendamustine composition.

FIG. 9A exemplarily illustrates a table showing a pre-lyophilization bendamustine composition VI.

FIG. 9B exemplarily illustrates a table showing a method for lyophilizing the pre-lyophilization bendamustine composition VI shown in FIG. 9A.

FIG. 9C exemplarily illustrates a table showing impurities generated during lyophilization of the pre-lyophilization bendamustine composition VI shown in FIG. 9A based on the steps of the method shown in FIG. 9B, and the reconstitution times of the lyophilized bendamustine composition.

FIG. 10A exemplarily illustrates a table showing a pre-lyophilization bendamustine composition VII.

FIG. 10B exemplarily illustrates a table showing a method for lyophilizing the pre-lyophilization bendamustine composition VII shown in FIG. 10A.

FIG. 10C exemplarily illustrates a table showing impurities generated during lyophilization of the pre-lyophilization bendamustine composition VII shown in FIG. 10A based on the steps of the method shown in FIG. 10B, and the reconstitution times of the lyophilized bendamustine composition.

DETAILED DESCRIPTION OF THE INVENTION

Figure 1:
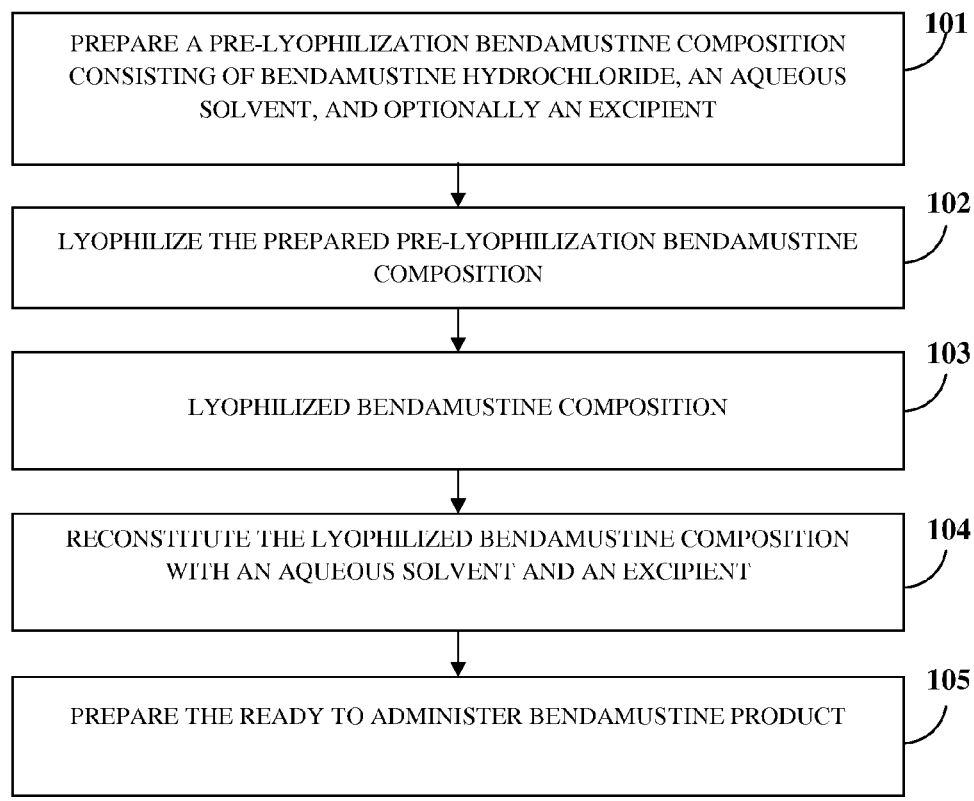
FIG. 1 exemplarily illustrates a method for preparing a ready to administer bendamustine product for treating a condition in a subject in need thereof.

FIG. 1 exemplarily illustrates a method for preparing a ready to administer bendamustine product for treating a condition in a subject, for example, a human or an animal, in need thereof. The method disclosed herein provides a composition of bendamustine in a stable lyophilized dosage form, where the lyophilized bendamustine composition is stable at room temperature for 6 months. The method disclosed herein is an aqueous based manufacturing process comprising a specific lyophilization cycle developed to yield a stable lyophilized bendamustine product which has a low level of impurities and is easily reconstitutable in about 30 seconds to about 60 seconds. In the method disclosed herein, a pre-lyophilization bendamustine composition is prepared 101 by mixing bendamustine hydrochloride, an aqueous solvent, and optionally an excipient. Bendamustine hydrochloride, herein referred to as "bendamustine", functions as a bifunctional alkylating agent. The chemical structure of bendamustine hydrochloride in the bendamustine composition is shown below:

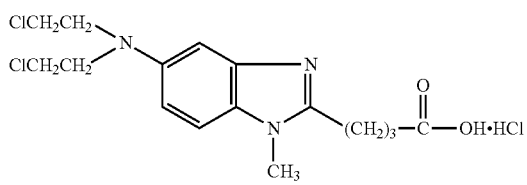

Bendamustine hydrochloride is 1H-benzimidazole-2-butanoic acid, 5-[bis(2-chloroethyl)amino]-1 methyl-, monohydrochloride. The empirical molecular formula of bendamustine hydrochloride is $C_{16}H_{21}Cl_2N_3O_2 \cdot HCl$. The molecular weight of bendamustine hydrochloride is 394.7. Bendamustine hydrochloride contains a mechlorethamine group and a benzimidazole heterocyclic ring with a butyric acid substituent. Bendamustine hydrochloride may be present in the lyophilized bendamustine composition in any suitable amount. In an embodiment, the bendamustine composition comprises bendamustine hydrochloride in a therapeutically effective amount to treat a condition, for example, cancer in a human subject or for diagnostic purposes. For example, bendamustine hydrochloride is present at a concentration of about 0.02 wt % to about 0.06 wt % by weight of the total ready to administer bendamustine composition.

Bendamustine is present in the prepared pre-lyophilization bendamustine composition at a concentration of, for example, about 0.01 wt % to about 90 wt % by weight of the prepared pre-lyophilization bendamustine composition. The pre-lyophilization bendamustine composition contains, for example, about 30 wt % to about 99.9 wt % by weight of the aqueous solvent based on the total weight of the prepared pre-lyophilization bendamustine composition. In an embodiment, the aqueous solvent comprises at least one of: about 30 wt % to about 99.5 wt % by weight of water, about 5 wt % to about 20 wt % by weight of an aqueous buffer, about 5 wt % to about 20 wt % by weight of saline, about 0.01 wt % to about 50 wt % by weight of at least one cryoprotectant, and about 0.01 wt % to about 50 wt % by weight of at least one aqueous soluble excipient based on the total weight of the aqueous solvent. The cryoprotectant comprises, for example, at least one of sucrose, trehalose, lactose, mannitol, sorbitol, colloidal silicon dioxide, maltose, polyvinylpyrrolidone, fructose, dextran, glycerol, polyvinyl alcohol, glycine, hydroxypropyl-β-cyclodextrin, gelatin, histidine, glycine, and any combination thereof. An excipient is a pharmacologically inactive substance, for example, a bulking agent, a filler, a diluent, etc., used to impart a function or a property to a formulation. The excipient is present in the prepared pre-lyophilization bendamustine composition at a concentration of, for example, about 0.01 wt % to about 50 wt % by weight of the pre-lyophilization bendamustine composition. The excipient comprises, for example, one of antioxidants, preservatives, stabilizers, mixtures, bulking agents, buffers, isotonicity agents, etc., and any combination thereof. The preservatives are, for example, phenol, thimerosal, chlorobutanol, benzyl alcohol, m-cresol, phenoxyethanol, methylparaben, propylparaben, etc. The bulking agents or cryoprotectants or lyoprotectants to facilitate lyophilization comprise, for example, amino acids such as lysine, alanine, glycine, etc.; polymers such as proteins and polyethylene glycol, polyvinylpyrrolidone, gelatin, dextran 40, albumin, etc. The isotonicity agents comprise, for example, sodium chloride, calcium chloride, potassium chloride, glycerol, thioglycerol, etc.

The antioxidants comprise hydrophobic antioxidants such as butylated hydroxytoluene, butylated hydroxyanisole, propyl gallate, α-tocopherol, tocopherol polyethylene glycol succinate (Vitamin E TPGS), L-cysteine, etc., and water soluble antioxidants such as sodium ethylenediaminetetraacetic acid (EDTA), thioglycerol, etc., and any combination thereof. In an embodiment, the concentration of antioxidants is, for example, about 0.005 wt % to about 5 wt % by weight of the pre-lyophilization bendamustine composition to improve stability of the pre-lyophilization bendamustine composition. In an embodiment, the buffers comprise, for example, citric acid, acetic acid, maleic acid, phosphoric acid, succinic acid, tartaric acid, counter ion salts, etc., and any combination thereof. The pH of the pre-lyophilization bendamustine composition is, for example, between 1 and 14. The pre-lyophilization bendamustine composition disclosed herein is free of a non-aqueous solvent, for example, organic solvents.

In an embodiment, the pre-lyophilization bendamustine composition is packaged in one or more containers, for example, vials, ampoules, etc., and other pharmaceutically acceptable containers. The pre-lyophilization bendamustine composition is prepared at a preset temperature between about −5° C. and about 15° C., below room temperature. In an embodiment, the pre-lyophilization bendamustine composition is prepared at a preset temperature of about −2° C. to about 15° C. For example, the pre-lyophilization bendamustine composition is prepared at a preset temperature of 1° C. In an embodiment, the manufacture of the bendamustine product from the pre-lyophilization step through the ready to administer bendamustine product is performed under aseptic conditions using aseptic procedures that are well known in the art. In an example, the prepared pre-lyophilization bendamustine composition consists of 0.5 wt % by weight of bendamustine hydrochloride, 98.65 wt % by weight of an aqueous solvent, and 0.85 wt % by weight of an excipient.

The prepared pre-lyophilization bendamustine composition is then lyophilized 102 to obtain a lyophilized bendamustine composition 103. Lyophilization, also referred to as freeze-drying, is a dehydration process at reduced temperatures and reduced pressures to preserve the pre-lyophilization bendamustine composition for an extended period of time and to allow the pre-lyophilization bendamustine composition to be more readily transported and/or administered to a subject. In an embodiment, the prepared pre-lyophilization bendamustine composition is lyophilized by freezing the prepared pre-lyophilization bendamustine composition at a preset temperature between about −20° C. and about −50° C. For example, in an embodiment, the prepared pre-lyophilization bendamustine composition is lyophilized by freezing the prepared pre-lyophilization bendamustine composition at a preset temperature of about −48° C.

In another embodiment, the prepared pre-lyophilization bendamustine composition is lyophilized by primary drying the prepared pre-lyophilization bendamustine composition at a preset temperature between about −10° C. and −35° C. For example, the prepared pre-lyophilization bendamustine composition is lyophilized by primary drying the prepared pre-lyophilization bendamustine composition at a preset temperature of about −30° C. The primary drying of the prepared pre-lyophilization bendamustine composition is carried out at a preset pressure, for example, between 50 millitorr (mTorr) and about 150 mTorr. For example, in an embodiment, the primary drying of the prepared pre-lyophilization bendamustine composition is carried out at a preset pressure of about 130 mTorr.

In an embodiment, the lyophilization of the prepared pre-lyophilization bendamustine composition comprises annealing of the prepared pre-lyophilization bendamustine composition at a preset temperature between about −60° C. and about −5° C. For example, in an embodiment, the prepared pre-lyophilization bendamustine composition is lyophilized by annealing the prepared pre-lyophilization bendamustine composition at a preset temperature of about −48° C. to about −10° C. The annealing of the prepared pre-lyophilization bendamustine composition is performed prior to and/or after freezing the prepared pre-lyophilization bendamustine composition. In an embodiment, the lyophilization of the prepared pre-lyophilization bendamustine composition comprises secondary drying of the prepared pre-lyophilization bendamustine composition at a preset temperature, for example, between about 15° C. and about 30° C. For example, in an embodiment, the prepared pre-lyophilization bendamustine composition is lyophilized by secondary drying the prepared pre-lyophilization bendamustine composition at a preset temperature of about 25° C.

The secondary drying of the prepared pre-lyophilization bendamustine composition is carried out at a preset pressure, for example, between 50 mTorr and about 150 mTorr. For example, in an embodiment, the secondary drying of the prepared pre-lyophilization bendamustine composition is carried out at a preset pressure of about 70 mTorr. In an embodiment, the lyophilization of the prepared pre-lyophilization bendamustine composition comprises condensed cooling and evacuation of the prepared pre-lyophilization bendamustine composition at a temperature, for example, between about −40° C. and about −55° C., for example, at a preset temperature of −48° C. prior to the primary drying of the prepared pre-lyophilization bendamustine composition. The prepared pre-lyophilization bendamustine composition is lyophilized, for example, into a cake, a powder, a solid concentrate, etc. The lyophilized bendamustine composition 103 comprises, for example, about 0.5 wt % to about 1 wt % by weight of any specified or unspecified impurity after lyophilization. The bendamustine product, after lyophilization, contains impurities at levels, for example, less than 2.5 wt %. For example, the lyophilized bendamustine product contains monohydroxy bendamustine at levels 0.0 wt % to 1.0 wt %, dihydroxy bendamustine at levels 0.0 wt % to 0.5 wt %, etc. The lyophilized bendamustine product is free of a non-aqueous solvent.

The lyophilized bendamustine composition 103 consists of bendamustine hydrochloride, an aqueous solvent, and optionally an excipient. The lyophilized bendamustine composition 103 contains bendamustine at a concentration of about 1 wt % to about 99 wt % by weight of the lyophilized bendamustine composition 103. In an embodiment, the lyophilized bendamustine composition 103 comprises about 0.1 wt % to about 0.5 wt % area percent of bendamustine, for example, about 0.45 wt % area percent of bendamustine. As used herein, the term "area percent" refers to a percent of a high performance liquid chromatography (HPLC) area of impurities with respect to bendamustine hydrochloride. The aqueous solvent is present at a concentration of about 0.01 wt % to about 5 wt % by weight of the lyophilized bendamustine composition 103. In an embodiment, the aqueous solvent comprises about 30 wt % to about 99.9 wt % by weight of water. In another embodiment, the aqueous solvent comprises at least one of an acid, a base, a salt, and about 1 wt % to about 99 wt % by weight of at least one aqueous soluble excipient. An excipient is present at a concentration of about 1 wt % to about 99 wt % by weight of the lyophilized bendamustine composition 103. The excipient comprises about 0.01 wt % to about 65 wt % by weight of at least one cryoprotectant. In an embodiment, the concentration of antioxidants is, for example, about 0.005 wt % to about 5 wt % by weight of the total lyophilized bendamustine composition 103 to improve stability of the lyophilized bendamustine composition 103.

In an example, for a 90%-110% assay, the lyophilized bendamustine composition 103 consists of about 0.33 wt % to about 0.41 wt % of bendamustine hydrochloride, about 0.57 wt % to about 0.69 wt % of mannitol, and about 0.1 wt % to about 2.5 wt % of water. In another example, the lyophilized bendamustine composition 103 consists of about 30 wt % to about 37 wt % by weight of bendamustine hydrochloride, 1.5 wt % to about 2.5 wt % by weight of an aqueous solvent, and about 55 wt % to about 70 wt % of an excipient based on the weight of the lyophilized bendamustine composition 103. The wt % of the aqueous solvent in the lyophilized bendamustine composition 103 is controlled within about 1%. In another example, a 25 mg/vial of the lyophilized bendamustine composition 103 consists of 25 mg of the bendamustine hydrochloride, 42.5 mg of the mannitol, and about 0.05 ml to 1.69 ml of water. In another example, a 100 mg/vial of the lyophilized bendamustine composition 103 consists of 100 mg of the bendamustine hydrochloride, 42.5 mg of mannitol, and about 0.25 ml to 6.8 ml of water. In another example, the lyophilized bendamustine composition 103 consists of 37 wt % of bendamustine hydrochloride, 63 wt % of mannitol, and about 0.1 wt %-2.5 wt % of water.

After the lyophilization step 102, the lyophilized bendamustine composition 103 is reconstituted 104 with an aqueous solvent, for example, water for injection and an excipient to produce a reconstituted bendamustine product at the desired bendamustine concentration, for example, at a bendamustine concentration of, for example, about 0.01 wt % to about 90.00 wt % based on the total weight of the reconstituted bendamustine composition. Embodiments of aqueous solvents are listed herein. Reconstitution of the lyophilized bendamustine composition 103 with the aqueous solvent is performed in about 30 seconds to about 300 seconds. For example, in an embodiment, the reconstitution of the lyophilized bendamustine composition 103 is performed in about 30 seconds to 60 seconds. The reconstituted bendamustine product contains an aqueous solvent at a concentration of, for example, about 30 wt % to about 99.9 wt % by weight of the reconstituted bendamustine product. An excipient is optionally present in the reconstituted bendamustine product at a concentration of, for example, about 0.01 wt % to about 50 wt % by weight of the reconstituted bendamustine product to increase the stability of the reconstituted bendamustine product. In an example, the reconstituted bendamustine product consists of 0.5 wt % by weight of bendamustine hydrochloride, 98.65 wt % by weight of an aqueous solvent, and 0.85 wt % by weight of an excipient.

The reconstituted bendamustine product comprises about 0.2 wt % to about 2.5 wt % by weight of one or more specified impurities and/or unspecified impurities. In an example, the reconstituted bendamustine product comprises unspecified impurities of about 0.2 wt % of the reconstituted bendamustine product. The specification for total allowable impurity of the lyophilized bendamustine product is 2.5 wt %, maximum. The reconstituted bendamustine product is diluted with a diluent to prepare 105 the ready to administer bendamustine product. The degradation, that is, the total impurities of the lyophilized bendamustine product at both the 3 month and 6 month stability testing period is within the permissible 2.5 wt % total impurity specification. The degradation of the lyophilized bendamustine product is between about 0.80 wt % and about 0.96 wt % when the lyophilized bendamustine product is stored for 3 months at 40° C. and 75% relative humidity (RH). The degradation of the lyophilized bendamustine product is between about 0.74 wt % and about 0.92 wt % when the lyophilized bendamustine product is stored for 3 months at 25° C. and 60% RH. The degradation of the lyophilized bendamustine product is between about 1.0 wt % and about 1.2 wt % when the lyophilized bendamustine product is stored for 6 months at 40° C. and 75% RH. The degradation of the lyophilized bendamustine product is between about 0.89 wt % and about 1.1 wt % when the lyophilized bendamustine product is stored for 6 months at 25° C. and 60% RH.

Figure 2:
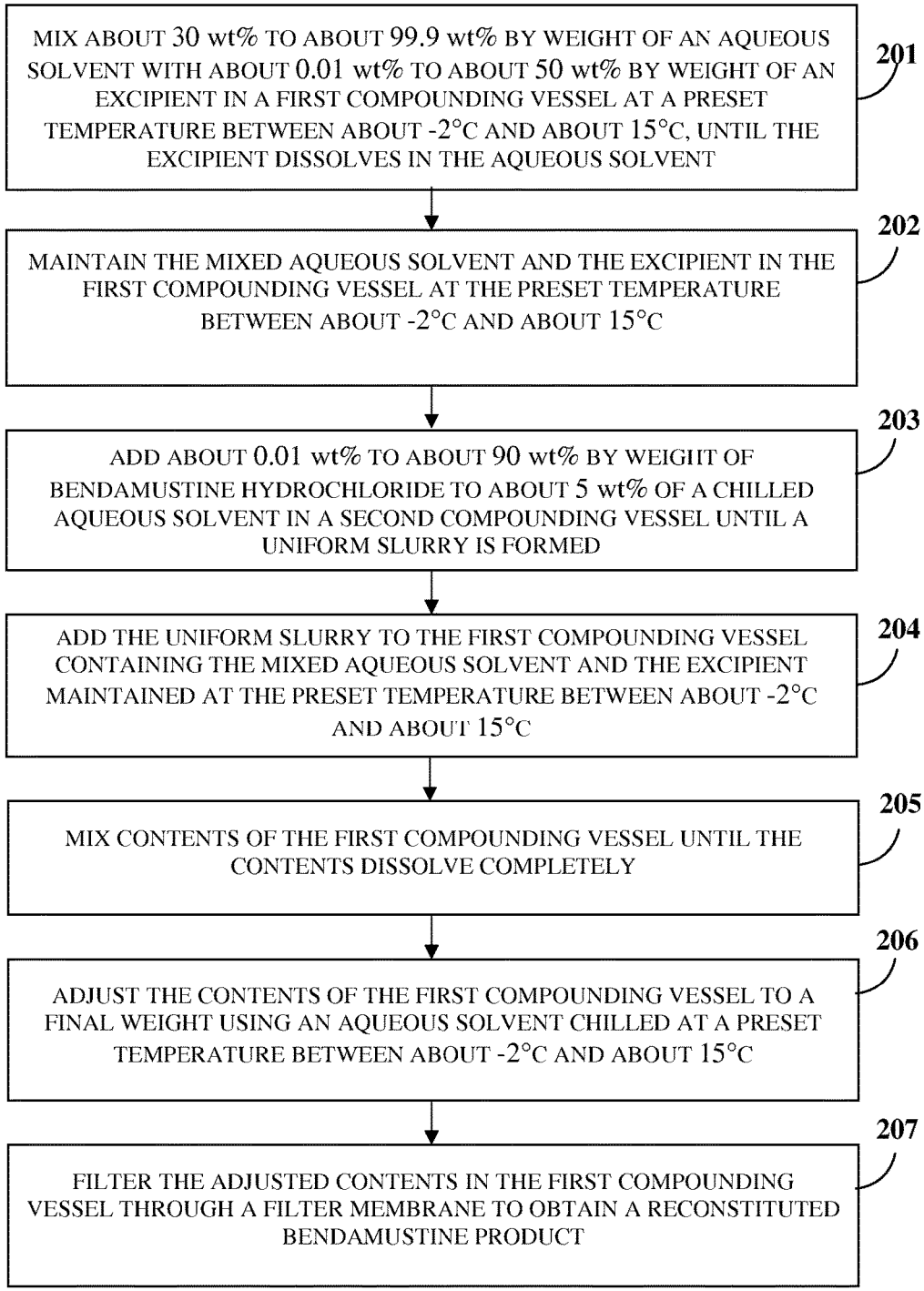
FIG. 2 exemplarily illustrates a method for reconstituting the lyophilized bendamustine product.

FIG. 2 exemplarily illustrates a method for reconstituting the lyophilized bendamustine product. About 30 wt % to about 99.9 wt % by weight of an aqueous solvent, for example, water for injection is mixed 201 with about 0.01 wt % to about 50 wt % by weight of an excipient, for example, mannitol in a first compounding vessel at a preset temperature, for example, between about −2° C. and about 15° C., until the excipient dissolves in the aqueous solvent, for example, in about 10 minutes. The mixed aqueous solvent and the excipient in the first compounding vessel are maintained 202 at the preset temperature between about −2° C. and about 15° C. in the aqueous solvent. About 0.01 wt % to about 90 wt % by weight of bendamustine hydrochloride is added 203 to about 5 wt % of a chilled aqueous solvent, for example, the chilled water for injection in a second compounding vessel and mixed for about 10 minutes until a uniform slurry is formed. The uniform slurry is then added 204 to the first compounding vessel containing the mixed aqueous solvent and the excipient maintained at the preset temperature between about −2° C. and about 15° C. The contents of the first compounding vessel are mixed 205, for example, for about 30 minutes to about 60 minutes until they dissolve completely. The temperature is maintained between about −2° C. and about 15° C. The contents of the first compounding vessel are then adjusted 206 to a final weight using an aqueous solvent chilled at a preset temperature between about −2° C. and about 15° C. In an embodiment, the preset temperature is maintained at about −2° C. to about 3° C. in the steps 201, 202, 204, and 206. The adjusted contents in the first compounding vessel are then filtered 207 through a filter membrane, for example, a 0.22 μm polyvinylidene difluoride (PVDF) membrane to obtain a reconstituted bendamustine product.

In an embodiment, the lyophilized bendamustine product is reconstituted as follows: In a pharmaceutically acceptable container, for example, a vial containing the lyophilized bendamustine product, a diluent, for example, water for injection, 0.9% sodium chloride, 2.5% dextrose/0.45% sodium chloride, etc., is injected in a quantity sufficient to obtain the desired bendamustine concentration. The contents of the container are swirled until the lyophilized bendamustine product dissolves, leaving no visible residue as undissolved matter, and the solution is not significantly less clear than the diluent, and essentially free from visible particles. In an embodiment, the reconstitution time of the lyophilized bendamustine product in accordance with this procedure is, for example, about 30 seconds to about 60 seconds. The reconstituted bendamustine product in the container is then transferred to an infusion bag for preparation of the ready to administer bendamustine product as recited below.

The reconstituted bendamustine product is transferred to an infusion bag at room temperature, for example, at about 15° C. to about 30° C. within 30 minutes after the lyophilized bendamustine composition is reconstituted. The reconstituted bendamustine product is diluted with a diluent, for example, 0.9% sodium chloride injection, 2.5% dextrose/0.45% sodium chloride injection, etc., to obtain the ready to administer, bendamustine solution which is stable for 24 hours when stored at about 2° C. to about 8° C., or stable for 3 hours when stored at room temperature, for example, at about 15° C. to about 30° C. under room lighting. Administration of the ready to administer bendamustine solution to a subject in need thereof must be completed within the above referenced 24 hour or 3 hour period.

The bendamustine hydrochloride is present in the ready to administer bendamustine product at a concentration of about 0.01 wt % to about 1 wt % by weight of the ready to administer bendamustine product with the balance of the composition consisting of an aqueous solvent and optionally an excipient. In an embodiment, the bendamustine hydrochloride is present in the ready to administer bendamustine product at a concentration of about 0.02 wt % to about 0.06 wt % by weight of the ready to administer bendamustine product with the balance of the composition consisting of an aqueous solvent and optionally an excipient. The ready to administer bendamustine product contains an aqueous solvent at a concentration of about 99 wt % to about 99.95 wt % by weight of the ready to administer bendamustine product. An excipient is optionally present in the ready to administer bendamustine product at a concentration of about 0.03 wt % to about 0.1 wt % by weight of the ready to administer bendamustine product. In an example, the ready to administer bendamustine product consists of 0.025 wt % by weight of bendamustine hydrochloride, 99.93 wt % by weight of an aqueous solvent, and 0.043 wt % by weight of an excipient based on the total weight of the ready to administer bendamustine product.

FIG. 3A exemplarily illustrates a table showing a pre-lyophilization bendamustine composition I. As exemplarily illustrated in FIG. 3A, the pre-lyophilization bendamustine composition I comprises 5 mg of bendamustine hydrochloride, 8.5 mg of mannitol, and about 1 ml of water. The pre-lyophilization bendamustine composition I is prepared by dissolving 5 mg bendamustine hydrochloride in water for injection containing mannitol at 3° C. The pre-lyophilization bendamustine composition I is maintained at about 0° C. to about 3° C., filled into vials, and then lyophilized using the steps of the method disclosed in the detailed description of FIG. 3B under aseptic conditions.

FIG. 3B exemplarily illustrates a table showing a method for lyophilizing the pre-lyophilization bendamustine composition I shown in FIG. 3A. Lyophilization of the pre-lyophilization bendamustine composition I comprises multiple steps: The pre-lyophilization bendamustine composition I is packaged in vials and loaded into a freeze dry system at a temperature less than about 3° C. A ramp function of the freeze dry system allows the temperature of the pre-lyophilization bendamustine composition I to be gradually increased or decreased. A hold function of the freeze dry system maintains the temperature of the pre-lyophilization bendamustine composition I at a particular temperature. The pre-lyophilization bendamustine composition I is first subjected to freezing starting at a temperature of about −48° C. for about 365 minutes. The temperature of the pre-lyophilization bendamustine composition I is then gradually increased to about −10° C. over a period of about 190 minutes using the ramp function. The hold function of the freeze dry system maintains the temperature of the pre-lyophilization bendamustine composition I at about −10° C. for about 180 minutes. The freezing temperature of the pre-lyophilization bendamustine composition I is then gradually decreased to about −48° C. over a period of about 190 minutes. The pre-lyophilization bendamustine composition I is then subjected to freezing at about −48° C. for about 180 minutes. The pre-lyophilization bendamustine composition I is then subjected to primary drying by gradually increasing the temperature to about −20° C. over a period of about 140 minutes. The pre-lyophilization bendamustine composition I is dried at about −20° C. for about 480 minutes. The pre-lyophilization bendamustine composition I is then subjected to secondary drying by gradually increasing the temperature to about +20° C. over a period of about 200 minutes. The pre-lyophilization bendamustine composition I is dried at about +20° C. for about 360 minutes. The atmospheric pressure maintained during the lyophilization process is, for example, 100 millitorr (mTorr) as exemplarily illustrated in FIG. 3B.

FIG. 4A exemplarily illustrates a table showing a pre-lyophilization bendamustine composition II. As exemplarily illustrated in FIG. 4A, the pre-lyophilization bendamustine composition II comprises 5 mg of bendamustine hydrochloride, 8.5 mg of mannitol, and about 1.0 ml water. The pre-lyophilization bendamustine composition II is prepared by dissolving bendamustine hydrochloride in water for injection containing mannitol at about 0° C. to 3° C. The pre-lyophilization bendamustine composition II is maintained at about 0° C. to about 3° C., filled into vials, and then lyophilized using the steps of the method disclosed in the detailed description of FIG. 4B under aseptic conditions.

FIG. 4B exemplarily illustrates a table showing a method for lyophilizing the pre-lyophilization bendamustine composition II shown in FIG. 4A. Lyophilization of the pre-lyophilization bendamustine composition II comprises multiple steps. The pre-lyophilization bendamustine composition II is packaged in the vials and loaded into a freeze dry system at a temperature less than about 3° C. The pre-lyophilization bendamustine composition II is first subjected to freezing starting at a temperature of about −48° C. for about 365 minutes. The temperature of the pre-lyophilization bendamustine composition II is gradually increased to about −10° C. over a period of about 190 minutes using the ramp function. The hold function of the freeze dry system maintains the temperature of the pre-lyophilization bendamustine composition II at about −10° C. for about 180 minutes. The freezing temperature of the pre-lyophilization bendamustine composition II is then gradually decreased to about −48° C. over a period of about 190 minutes. The pre-lyophilization bendamustine composition II is then subjected to freezing at about −48° C. for about 180 minutes. The pre-lyophilization bendamustine composition II is then subjected to primary drying by gradually increasing the temperature to about −20° C. in about 140 minutes. The pre-lyophilization bendamustine composition II is then dried at about −20° C. for about 480 minutes. The pre-lyophilization bendamustine composition II is then subjected to secondary drying by gradually increasing the temperature to about 25° C. over a period of about 200 minutes. The pre-lyophilization bendamustine composition II is dried at about 25° C. for about 360 minutes. The atmospheric pressure maintained during the lyophilization process is, for example, 100 mTorr as exemplarily illustrated in FIG. 4B.

FIG. 5 exemplarily illustrates a table showing impurities generated during lyophilization of the pre-lyophilization bendamustine compositions I and II shown in FIG. 3A and FIG. 4A respectively, based on the steps of the methods shown in FIG. 3B and FIG. 4B respectively, and the reconstitution times of the corresponding lyophilized bendamustine compositions I and II respectively. The impurities generated during lyophilization of the pre-lyophilization bendamustine composition I and the pre-lyophilization bendamustine composition II disclosed in the detailed description of FIG. 3A and FIG. 4A respectively are, for example, bendamustine monohydrate, bendamustine dihydrate, etc. The percentage concentrations of bendamustine monohydrate generated during lyophilization of the pre-lyophilization bendamustine compositions I and II are 0.25 and 0.30 respectively. The percentage concentration of bendamustine dihydrate generated during lyophilization of the pre-lyophilization bendamustine composition I is below a detection limit, while no bendamustine dihydrate is generated during lyophilization of the pre-lyophilization bendamustine composition II. The reconstitution times for reconstituting the lyophilized bendamustine compositions for administering to a subject in need thereof is, for example, less than 1 minute, for example, about 30 seconds to about 60 seconds as exemplarily illustrated in FIG. 5. As used herein, the term "reconstitution time" refers to the time required to rehydrate and dissolve the lyophilized bendamustine product in an aqueous solvent or a diluent.

FIG. 6A exemplarily illustrates a table showing a pre-lyophilization bendamustine composition III. As exemplarily illustrated in FIG. 6A, the pre-lyophilization bendamustine composition III comprises 5 mg of bendamustine hydrochloride, 8.5 mg of mannitol, and about 1 ml of water. The pre-lyophilization bendamustine composition III is prepared by dissolving bendamustine hydrochloride in water for injection containing mannitol at about 0° C. to 3° C. The pre-lyophilization bendamustine composition III is maintained at about 0° C. to about 3° C., filled into vials, and then lyophilized using the steps of the method disclosed in the detailed description of FIG. 6B under aseptic conditions. The final lyophilized bendamustine product has 100 mg/vial of bendamustine hydrochloride.

FIG. 6B exemplarily illustrates a table showing a method for lyophilizing the pre-lyophilization bendamustine composition III shown in FIG. 6A. The lyophilization of the pre-lyophilization bendamustine composition III comprises multiple steps. The pre-lyophilization bendamustine composition III packaged in a vial is loaded into a freeze dry system at a temperature less than about 3° C. The pre-lyophilization bendamustine composition III is first subjected to freezing by gradually decreasing the freezing temperature of the pre-lyophilization bendamustine composition III to about −48° C. over a period of about 100 minutes using the ramp function of the freeze dry system. The hold function of the freeze dry system maintains the temperature of the pre-lyophilization bendamustine composition III at about −48° C. for about 180 minutes. The pre-lyophilization bendamustine composition III is then subjected to annealing by gradually increasing the temperature to about −10° C. over a period of about 76 minutes. The pre-lyophilization bendamustine composition III is annealed at about −10° C. for about 180 minutes. The pre-lyophilization bendamustine composition III is again subjected to freezing by gradually decreasing the temperature to about −48° C. over a period of about 76 minutes. The pre-lyophilization bendamustine composition III freezes at about −48° C. for about 240 minutes. The pre-lyophilization bendamustine composition III is then subjected to primary drying by gradually increasing the temperature to about −20° C. over a period of about 140 minutes. The pre-lyophilization bendamustine composition III is dried at about −20° C. for about 720 minutes. The pre-lyophilization bendamustine composition III is then subjected to secondary drying by gradually increasing the temperature to about +25° C. over a period of about 225 minutes. The pre-lyophilization bendamustine composition III is dried at about +25° C. for about 480 minutes. The atmospheric pressure maintained during the primary drying and the secondary drying of the lyophilization process is, for example, 100 mTorr as exemplarily illustrated in FIG. 6B.

FIG. 6C exemplarily illustrates a table showing impurities generated during lyophilization of the pre-lyophilization bendamustine composition III shown in FIG. 6A based on the steps of the method shown in FIG. 6B, and the reconstitution times of the lyophilized bendamustine composition. The impurities generated during lyophilization of the pre-lyophilization bendamustine composition III disclosed in the detailed description of FIG. 6A are, for example, bendamustine monohydrate, bendamustine dihydrate, etc. The percentage concentration of bendamustine monohydrate generated during lyophilization of the pre-lyophilization bendamustine composition III is 0.52. The percentage concentration of bendamustine dihydrate generated during lyophilization of the pre-lyophilization bendamustine composition III is below a detection limit. The reconstitution time for reconstituting the lyophilized bendamustine composition for administering to a subject in need thereof is less than 2 minutes, for example, about 30 seconds to about 90 seconds as exemplarily illustrated in FIG. 6C.

FIG. 7A exemplarily illustrates a table showing a pre-lyophilization bendamustine composition IV. As exemplarily illustrated in FIG. 7A, the pre-lyophilization bendamustine composition IV comprises 5 mg of bendamustine hydrochloride, 8.5 mg of mannitol, and about 1.0 ml water. A lab scale batch of about 500 mL of the pre-lyophilization bendamustine composition IV sufficient for 100 vials of 25 mg/vial is prepared by dissolving bendamustine hydrochloride in water for injection containing mannitol at about 0° to 3° C. The pre-lyophilization bendamustine composition IV is maintained at about 0° C. to 3° C., filled into vials, and then lyophilized using the steps of the method shown in FIG. 7B under aseptic conditions. 5 mL of the pre-lyophilization bendamustine composition IV is filled in 10 mL vials and lyophilized using the steps of the method disclosed in the detailed description of FIG. 7B.

FIG. 7B exemplarily illustrates a table showing a method for lyophilizing the pre-lyophilization bendamustine composition IV shown in FIG. 7A. Lyophilization of the pre-lyophilization bendamustine composition IV comprises multiple steps. The pre-lyophilization bendamustine composition IV is packaged in the vials and loaded into a freeze dry system at a temperature less than about 3° C. The pre-lyophilization bendamustine composition IV is first subjected to freezing by gradually decreasing the freezing temperature of the pre-lyophilization bendamustine composition IV to about −48° C. over a period of about 100 minutes using the ramp function of the freeze dry system. The hold function of the freeze dry system maintains the temperature of the pre-lyophilization bendamustine composition IV at about −48° C. for about 180 minutes. The pre-lyophilization bendamustine composition IV is then subjected to annealing by gradually increasing the temperature to about −10° C. over a period of about 76 minutes. The pre-lyophilization bendamustine composition IV is annealed at about −10° C. for about 180 minutes. The pre-lyophilization bendamustine composition IV is again subjected to freezing by gradually decreasing the temperature to about −48° C. over a period of about 76 minutes. The pre-lyophilization bendamustine composition IV freezes at about −48° C. for about 240 minutes. The pre-lyophilization bendamustine composition IV is then subjected to primary drying by gradually increasing the temperature to about −20° C. over a period of about 140 minutes. The pre-lyophilization bendamustine composition IV is dried at about −20° C. for about 720 minutes. The pre-lyophilization bendamustine composition IV is then subjected to secondary drying by gradually increasing the temperature to about 25° C. over a period of about 225 minutes. The pre-lyophilization bendamustine composition IV is dried at about 25° C. for about 480 minutes. The atmospheric pressure maintained during the freezing, the primary drying, and the secondary drying of the lyophilization process is, for example, 100 mTorr as exemplarily illustrated in FIG. 7B.

FIG. 7C exemplarily illustrates a table showing impurities generated during lyophilization of the pre-lyophilization bendamustine composition IV shown in FIG. 7A based on the steps of the method shown in FIG. 7B, and the reconstitution times of the lyophilized bendamustine composition. The results of physical and chemical characterization of an initial time point and stability samples of the pre-lyophilization bendamustine composition IV shown in FIG. 7A, evaluated at ambient and accelerated conditions are also exemplarily illustrated in FIG. 7C. The table exemplarily illustrated in FIG. 7C shows a comparison of stability results for bendamustine hydrochloride, a lyophilized bendamustine powder for injection, and a 25 mg/vial. The impurities generated during the lyophilization of the pre-lyophilization bendamustine composition IV disclosed in the detailed description of FIG. 7A are, for example, monohydroxy-bendamustine hydrochloride, dihydroxy-bendamustine hydrochloride, etc. The percentage concentration of monohydroxy-bendamustine hydrochloride generated during lyophilization of the pre-lyophilization bendamustine composition IV is 0.49, while dihydroxy-bendamustine hydrochloride is not detected.

The bendamustine product, after lyophilization, appears as a white lyophilized cake. A stability analysis on the lyophilized bendamustine composition was conducted. The stability analysis of the lyophilized bendamustine composition helps determine the quality of the lyophilized bendamustine composition when subjected to different ambient conditions. The lyophilized bendamustine composition is subjected to varying temperatures and humidity for an extended period. For example, the lyophilized bendamustine composition is subjected to 25±3° C./60±5% relative humidity (RH) for a period of 1 month, 3 months, etc. The lyophilized bendamustine composition retains the appearance of white lyophilized cake even after being subjected to a temperature/humidity level of 25±3° C./60±5% RH for a period of 1 month. The percentage concentration of monohydroxy-bendamustine hydrochloride, after subjecting the lyophilized bendamustine composition to the stability analysis, is 0.47, while dihydroxy-bendamustine hydrochloride is not detected. The lyophilized bendamustine composition still retains the appearance of a white lyophilized cake even after being subjected to a temperature/humidity level of 25±3° C./60±5% RH for a period of 3 months. The percentage concentration of monohydroxy-bendamustine hydrochloride, after subjecting the lyophilized bendamustine composition to the stability analysis, is 0.57, while dihydroxy-bendamustine hydrochloride is not detected.

In another example, the lyophilized bendamustine composition disclosed in the detailed description of FIG. 7A, is subjected to 40±3° C./75±5% RH for a period of 1 month, 2 months, 3 months, etc. The lyophilized bendamustine composition retains the appearance of a white lyophilized cake even after being subjected to a temperature/humidity level of 40±3° C./75±5% RH for a period of 1 month. The percentage concentration of monohydroxy-bendamustine hydrochloride, after subjecting the lyophilized bendamustine composition to the stability analysis, is 0.45, while dihydroxy-bendamustine hydrochloride is not detected. The lyophilized bendamustine composition still retains the appearance of a white lyophilized cake even after being subjected to a temperature/humidity level of 40±3° C./75±5% RH for a period of 2 months. The percentage concentration of monohydroxy-bendamustine hydrochloride, after subjecting the lyophilized bendamustine composition to the stability analysis, is 0.52, while dihydroxy-bendamustine hydrochloride is not detected. The lyophilized bendamustine composition still retains the appearance of a white lyophilized cake even after being subjected to a temperature/humidity level of 40±3° C./75±5% RH for a period of 3 months. The percentage concentration of monohydroxy-bendamustine hydrochloride, after subjecting the lyophilized bendamustine composition to the stability analysis, is 0.55, while dihydroxy-bendamustine hydrochloride is not detected. The reconstitution time of the lyophilized bendamustine composition varies, for example, from 30 seconds to 45 seconds. The reconstitution time of the lyophilized bendamustine composition subjected to the stability analysis for administering the lyophilized bendamustine composition to a subject in need thereof varies, for example, from 30 seconds to 45 seconds, 30 seconds to 60 seconds, etc. A relative retention time (RRT) for an unknown impurity or an unspecified impurity is also calculated as exemplarily illustrated in FIG. 7C. The RRT of the unknown impurity or the unspecified impurity is less than the smallest detectable concentration or the limit of quantitation (LOQ). Furthermore, as exemplarily illustrated in FIG. 7C, the total percentage of impurities in the final bendamustine composition, after lyophilization and reconstitution, is less than 1 wt %.

FIG. 8A exemplarily illustrates a table showing a pre-lyophilization bendamustine composition V. As exemplarily illustrated in FIG. 8A, the pre-lyophilization bendamustine composition V comprises 5 mg of bendamustine hydrochloride, 8.5 mg of mannitol, and about 1.0 ml water. A lab scale batch of 500 mL of the pre-lyophilization bendamustine composition V sufficient for 25 vials of 100 mg/vial is prepared by dissolving bendamustine hydrochloride in water for injection containing mannitol at about 0° C. to 3° C. The pre-lyophilization bendamustine composition V is maintained at about 0° C. to 3° C. 25 mL pre-lyophilization bendamustine composition V is filled into 30 mL vials and then lyophilized using the steps of the method disclosed in the detailed description of FIG. 8B under aseptic conditions.

FIG. 8B exemplarily illustrates a table showing a method for lyophilizing the pre-lyophilization bendamustine composition V shown in FIG. 8A. Lyophilization of the pre-lyophilization bendamustine composition V comprises multiple steps. The pre-lyophilization bendamustine composition V is packaged in the vials and loaded into a freeze dry system at a temperature less than about 3° C. The pre-lyophilization bendamustine composition V is first subjected to freezing by gradually decreasing the freezing temperature of the pre-lyophilization bendamustine composition V to about −48° C. over a period of about 100 minutes using the ramp function of the freeze dry system. The hold function of the freeze dry system maintains the temperature of the pre-lyophilization bendamustine composition V at about −48° C. for about 180 minutes. The pre-lyophilization bendamustine composition V is then subjected to annealing by gradually increasing the temperature to about −10° C. over a period of about 76 minutes. The pre-lyophilization bendamustine composition V is annealed at about −10° C. for about 180 minutes. The pre-lyophilization bendamustine composition V is again subjected to freezing by gradually decreasing the temperature to about −48° C. over a period of about 76 minutes. The pre-lyophilization bendamustine composition V freezes at about −48° C. for about 240 minutes. The pre-lyophilization bendamustine composition V is then subjected to primary drying by gradually increasing the temperature to about −20° C. over a period of about 140 minutes. The pre-lyophilization bendamustine composition V is dried at about −20° C. for about 720 minutes. The pre-lyophilization bendamustine composition V is then subjected to secondary drying by gradually increasing the temperature to about +25° C. over a period of about 225 minutes. The pre-lyophilization bendamustine composition V is dried at about +25° C. for about 480 minutes. The atmospheric pressure maintained during the freezing, the primary drying, and the secondary drying of the lyophilization process is, for example, 100 mTorr as exemplarily illustrated in FIG. 8B.

FIG. 8C exemplarily illustrates a table showing impurities generated during lyophilization of the pre-lyophilization bendamustine composition V shown in FIG. 8A based on the steps of the method shown in FIG. 8B, and the reconstitution times of the lyophilized bendamustine composition. Results of physical and chemical characterization of an initial time point and stability samples of the pre-lyophilization bendamustine composition V shown in FIG. 8A, evaluated at ambient and accelerated conditions are also exemplarily illustrated in FIG. 8C. The table exemplarily illustrated in FIG. 8C shows a comparison of stability results for bendamustine hydrochloride, a lyophilized bendamustine powder for injection, and a 100 mg/vial. The impurities generated during lyophilization of the pre-lyophilization bendamustine composition V as disclosed in the detailed description of FIG. 8A are, for example, monohydroxy-bendamustine hydrochloride, dihydroxy-bendamustine hydrochloride, etc. The percentage concentration of monohydroxy-bendamustine hydrochloride generated during lyophilization of the pre-lyophilization bendamustine composition V is 0.45, while dihydroxy-bendamustine hydrochloride is not detected. The lyophilized bendamustine composition, after lyophilization, appears as a white lyophilized cake. A stability analysis on the lyophilized bendamustine composition is conducted. The lyophilized bendamustine composition is subjected to varying temperatures and humidity for an extended period. For example, the lyophilized bendamustine composition is subjected to 25±3° C./60±5% relative humidity (RH) for a period of 1 month, 3 months, etc. The lyophilized bendamustine composition retains the appearance of a white lyophilized cake even after being subjected to a temperature/humidity level of 25±3° C./60±5% RH for a period of 1 month. The percentage concentration of monohydroxy-bendamustine hydrochloride, after subjecting the lyophilized bendamustine composition to the stability analysis, is 0.43, while dihydroxy-bendamustine hydrochloride is not detected. The lyophilized bendamustine composition still retains the appearance of a white lyophilized cake even after being subjected to a temperature/humidity level of 25±3° C./60±5% RH for a period of 3 months. The percentage concentration of monohydroxy-bendamustine hydrochloride, after subjecting the lyophilized bendamustine composition to the stability analysis, is 0.53, while dihydroxy-bendamustine hydrochloride is not detected.

In another example, the lyophilized bendamustine composition disclosed in the detailed description of FIG. 8A is subjected to a temperature/humidity level of 40±3° C./75±5% RH for a period of 1 month, 2 months, 3 months, etc. The lyophilized bendamustine composition retains the appearance of a white lyophilized cake even after being subjected to a temperature/humidity level of 40±3° C./75±5% RH for a period of 1 month. The percentage concentration of monohydroxy-bendamustine hydrochloride, after subjecting the lyophilized bendamustine composition to the stability analysis, is 0.43, while dihydroxy-bendamustine hydrochloride is not detected. The lyophilized bendamustine composition still retains the appearance of a white lyophilized cake even after being subjected to a temperature/humidity level of 40±3° C./75±5% RH for a period of 2 months. The percentage concentration of monohydroxy-bendamustine hydrochloride, after subjecting the lyophilized bendamustine composition to the stability analysis, is 0.53, while dihydroxy-bendamustine hydrochloride is not detected. The lyophilized bendamustine composition still retains the appearance of a white lyophilized cake even after being subjected to a temperature/humidity level of 40±3° C./75±5% RH for a period of 3 months. The percentage concentration of monohydroxy-bendamustine hydrochloride, after subjecting the lyophilized bendamustine composition to the stability analysis, is 0.51, while dihydroxy-bendamustine hydrochloride is not detected. The reconstitution time of the lyophilized bendamustine composition varies from 90 seconds to 120 seconds. The reconstitution time of the lyophilized bendamustine composition subjected to the stability analysis for administering the lyophilized bendamustine composition into a subject in need thereof varies, for example, from 90 seconds to 120 seconds. A relative retention time (RRT) for an unknown impurity is also calculated as exemplarily illustrated in FIG. 8C. The RRT of the unknown or unspecified impurity is less than the smallest detectable concentration or the limit of quantitation (LOQ). Furthermore, as exemplarily illustrated in FIG. 8C, the total percentage of impurities in the final bendamustine composition, after lyophilization and reconstitution, is less than 1 wt %.

FIG. 9A exemplarily illustrates a table showing a pre-lyophilization bendamustine composition VI. As exemplarily illustrated in FIG. 9A, the pre-lyophilization bendamustine composition VI comprises 5 mg of bendamustine hydrochloride, 8.5 mg of mannitol, and about 1.0 ml water. A lab scale batch of 30 liters (L) of the pre-lyophilization bendamustine composition VI sufficient for 6000 vials of 25 mg/vial is prepared by dissolving bendamustine hydrochloride in water for injection containing mannitol at about 0° C. to 3° C. The pre-lyophilization bendamustine composition VI is maintained at about 0° C. to 3° C. 5 mL pre-lyophilization bendamustine composition VI is filled in an 8 mL vial and then lyophilized using the steps of the method disclosed in the detailed description of FIG. 9B under aseptic conditions.

FIG. 9B exemplarily illustrates a table showing a method for lyophilizing the pre-lyophilization bendamustine composition VI shown in FIG. 9A. Lyophilization of the pre-lyophilization bendamustine composition VI comprises multiple steps. The pre-lyophilization bendamustine composition VI is packaged in a vial and loaded onto a freeze dry system at a temperature of about 0° C. The pre-lyophilization bendamustine composition VI is first subjected to freezing at about 0° C. for about 10 minutes. The freezing temperature of the pre-lyophilization bendamustine composition VI is gradually decreased to about −48° C. over a period of about 60 minutes using the ramp function of the freeze dry system. The hold function of the freeze dry system maintains the temperature of the pre-lyophilization bendamustine composition VI at about −48° C. for about 180 minutes. The pre-lyophilization bendamustine composition VI is then subjected to annealing by gradually increasing the temperature to about −10° C. over a period of about 70 minutes. The pre-lyophilization bendamustine composition VI is annealed at about −10° C. for about 180 minutes. The pre-lyophilization bendamustine composition VI is again subjected to freezing by gradually decreasing the temperature to about −48° C. over a period of about 40 minutes. The pre-lyophilization bendamustine composition VI freezes at about −48° C. for about 240 minutes. The pre-lyophilization bendamustine composition VI is then passed through a condenser cooling and evacuation chamber. The pre-lyophilization bendamustine composition VI is then subjected to primary drying by gradually increasing the temperature to about −20° C. over a period of about 140 minutes. The pre-lyophilization bendamustine composition VI is dried at about −20° C. for about 1440 minutes. The pre-lyophilization bendamustine composition VI is then subjected to secondary drying by gradually increasing the temperature to about 25° C. over a period of about 255 minutes. The pre-lyophilization bendamustine composition VI is dried at about 25° C. for about 1440 minutes. The atmospheric pressure maintained during the primary drying and the secondary drying of the lyophilization process is, for example, 100 mTorr as exemplarily illustrated in FIG. 9B.

FIG. 9C exemplarily illustrates a table showing impurities generated during lyophilization of the pre-lyophilization bendamustine composition VI shown in FIG. 9A based on the steps of the method shown in FIG. 9B, and the reconstitution times of the lyophilized bendamustine composition. The table exemplarily illustrated in FIG. 9C shows a comparison of stability results for bendamustine hydrochloride, a lyophilized bendamustine powder for injection, and a 100 mg/vial. Results of physical and chemical characterization of an initial time point and stability samples of the pre-lyophilization bendamustine composition VI shown in FIG. 9A evaluated at ambient and accelerated conditions are also exemplarily illustrated in FIG. 9C. The table exemplarily illustrated in FIG. 9C shows a comparison of stability results of a scale up batch of 25 mg. The impurities generated during lyophilization of the pre-lyophilization bendamustine composition VI as disclosed in the detailed description of FIG. 9A are, for example, monohydroxy-bendamustine hydrochloride, dihydroxy-bendamustine hydrochloride, etc. The percentage concentration of monohydroxy-bendamustine hydrochloride generated during lyophilization of the pre-lyophilization bendamustine composition VI is 0.78, while dihydroxy-bendamustine hydrochloride is not detected. The lyophilized bendamustine composition, after lyophilization, appears as a white lyophilized powder. A stability analysis on the lyophilized bendamustine composition is conducted. The lyophilized bendamustine composition is subjected to varying temperatures and humidity for an extended period. For example, the lyophilized bendamustine composition is subjected to 25° C./60% relative humidity (RH) for a period of 1 month or 4 weeks. The lyophilized bendamustine composition retains the appearance of a white lyophilized powder even after being subjected to a temperature/humidity level of 25° C./60% RH for a period of 1 month. The percentage concentration of monohydroxy-bendamustine hydrochloride, after subjecting the lyophilized bendamustine composition to the stability analysis, is 0.81, while dihydroxy-bendamustine hydrochloride is not detected. The lyophilized bendamustine composition still retains the appearance of a white lyophilized powder even after being subjected to a temperature/humidity level of 40° C./75% RH for a period of 1 month. The percentage concentration of monohydroxy-bendamustine hydrochloride, after subjecting the lyophilized bendamustine composition to the stability analysis, is 0.68, while dihydroxy-bendamustine hydrochloride is not detected.

In another example, the lyophilized bendamustine composition disclosed in the detailed description of FIG. 9A is subjected to 40° C./75% RH for a period of 2 months or 8 weeks. The lyophilized bendamustine composition retains the appearance of a white lyophilized powder even after being subjected to a temperature/humidity level of 40° C./75% RH for a period of 2 months. The percentage concentration of the impurity, for example, monohydroxy-bendamustine hydrochloride, after subjecting the lyophilized bendamustine composition to the stability analysis, is 0.66, while dihydroxy-bendamustine hydrochloride is not detected.

In another example, the lyophilized bendamustine composition disclosed in the detailed description of FIG. 9A is subjected to 25° C./60% RH for a period of 3 months or 12 weeks. The lyophilized bendamustine composition retains the appearance of a white lyophilized powder even after being subjected to a temperature/humidity level of 25° C./60% RH for a period of 3 months. The percentage concentration of monohydroxy-bendamustine hydrochloride, after subjecting the lyophilized bendamustine composition to the stability analysis, is 0.74, while dihydroxy-bendamustine hydrochloride is not detected. The lyophilized bendamustine composition still retains the appearance of a white lyophilized powder even after being subjected to a temperature/humidity level of 40° C./75% RH for a period of 3 months. The percentage concentration of monohydroxy-bendamustine hydrochloride, after subjecting the lyophilized bendamustine composition to the stability analysis, is 0.69, while dihydroxy-bendamustine hydrochloride is not detected. The reconstitution time of the lyophilized bendamustine composition is less than 1 minute. The reconstitution time of the lyophilized bendamustine composition subjected to stability analysis for administering the lyophilized bendamustine composition to a subject is also less than 1 minute. The appearance of the reconstituted bendamustine composition is that of a solution free from visible particles of foreign matter. Furthermore, as exemplarily illustrated in FIG. 9C, the total percentage of impurities in the final bendamustine composition, after lyophilization and reconstitution, is less than 1 wt %.

FIG. 10A exemplarily illustrates a table showing a pre-lyophilization bendamustine composition VII. As exemplarily illustrated in FIG. 10A, the pre-lyophilization bendamustine composition VII comprises 5 mg of bendamustine hydrochloride, 8.5 mg of mannitol, and about 1.0 ml water. A lab scale batch of 30 liters of the pre-lyophilization bendamustine composition VII sufficient for 1500 vials of 100 mg/vial is prepared by dissolving bendamustine hydrochloride in water for injection containing mannitol at about −2° C. to 3° C. The pre-lyophilization bendamustine composition VII is maintained at about 0° C. to 3° C. 25 mL pre-lyophilization bendamustine composition VII is filled into a 30 mL vial and then lyophilized using the steps of the method disclosed in the detailed description of FIG. 10B under aseptic conditions.

FIG. 10B exemplarily illustrates a table showing a method for lyophilizing the pre-lyophilization bendamustine composition VII shown in FIG. 10A. Lyophilization of the pre-lyophilization bendamustine composition VII comprises multiple steps. The pre-lyophilization bendamustine composition VII is packaged in the vials and loaded into a freeze dry system at a temperature of about 0° C. The pre-lyophilization bendamustine composition VII is first subjected to freezing at about 0° C. for about 10 minutes. The freezing temperature of the pre-lyophilization bendamustine composition VII is gradually decreased to about −48° C. over a period of about 56 minutes using the ramp function of the freeze dry system. The hold function of the freeze dry system maintains the temperature of the pre-lyophilization bendamustine composition VII at about −48° C. for about 180 minutes. The pre-lyophilization bendamustine composition VII is then subjected to annealing by gradually increasing the temperature to about −10° C. over a period of about 84 minutes. The pre-lyophilization bendamustine composition VII is annealed at about −10° C. for about 180 minutes. The pre-lyophilization bendamustine composition VII is again subjected to freezing by gradually decreasing the temperature to about −48° C. over a period of about 43 minutes. The pre-lyophilization bendamustine composition VII is subjected to freezing at about −48° C. for about 240 minutes. The pre-lyophilization bendamustine composition VII is then passed through a condenser cooling and evacuation chamber. The pre-lyophilization bendamustine composition VII is then subjected to primary drying by gradually increasing the temperature to about −20° C. over a period of about 162 minutes. The pre-lyophilization bendamustine composition VII is dried at about −20° C. for about 1500 minutes. The pre-lyophilization bendamustine composition VII is then subjected to secondary drying by gradually increasing the temperature to about 25° C. over a period of about 253 minutes. The pre-lyophilization bendamustine composition VII is dried at about 25° C. for about 2622 minutes. The atmospheric pressure maintained during the condensing and cooling, the primary drying, and the secondary drying of the lyophilization process is, for example, 100 mTorr as exemplarily illustrated in FIG. 10B.

FIG. 10C exemplarily illustrates a table showing impurities generated during lyophilization of the pre-lyophilization bendamustine composition VII shown in FIG. 10A based on the steps of the method shown in FIG. 10B, and the reconstitution times of the lyophilized bendamustine composition. The impurities generated during the lyophilization of the pre-lyophilization bendamustine composition VII as disclosed in the detailed description of FIG. 10A are, for example, monohydroxy-bendamustine hydrochloride, dihydroxy-bendamustine hydrochloride, etc. The percentage concentration of monohydroxy-bendamustine hydrochloride generated during lyophilization of the pre-lyophilization bendamustine composition VII is 0.84, while dihydroxy-bendamustine hydrochloride is not detected. The lyophilized bendamustine composition, after lyophilization, appears as a white lyophilized powder. A stability analysis on the lyophilized bendamustine composition is conducted. The lyophilized bendamustine composition is subjected to varying temperatures and humidity for an extended period. For example, the lyophilized bendamustine composition is subjected to 25° C./60% relative humidity (RH) for a period of 1 month or 4 weeks. The lyophilized bendamustine composition retains the appearance of a white lyophilized powder even after being subjected to a temperature/humidity level of 25° C./60% RH for a period of 1 month. The percentage concentration of monohydroxy-bendamustine hydrochloride, after subjecting the lyophilized bendamustine composition to the stability analysis, is 0.83, while dihydroxy-bendamustine hydrochloride is not detected. The lyophilized bendamustine composition still retains the appearance of a white lyophilized powder even after being subjected to a temperature/humidity level of 40° C./75% RH for a period of 1 month. The percentage concentration of monohydroxy-bendamustine hydrochloride, after subjecting the lyophilized bendamustine composition to the stability analysis, is 0.94, while dihydroxy-bendamustine hydrochloride is not detected.

In another example, the lyophilized bendamustine composition disclosed in the detailed description of FIG. 10A is subjected to 40° C./75% RH for a period of 2 months or 8 weeks. The lyophilized bendamustine composition retains the appearance of a white lyophilized powder even after being subjected to a temperature/humidity level of 40° C./75% RH for a period of 2 months. The percentage concentration of monohydroxy-bendamustine hydrochloride, after subjecting the lyophilized bendamustine composition to the stability analysis, is 0.93, while dihydroxy-bendamustine hydrochloride is not detected.

In another example, the lyophilized bendamustine composition disclosed in the detailed description of FIG. 10A is subjected to 25° C./60% RH for a period of 3 months or 12 weeks. The lyophilized bendamustine composition retains the appearance of a white lyophilized powder even after being subjected to a temperature/humidity level of 25° C./60% RH for a period of 3 months. The percentage concentration of monohydroxy-bendamustine hydrochloride, after subjecting the lyophilized bendamustine composition to the stability analysis, is 0.92, while dihydroxy-bendamustine hydrochloride is not detected. The lyophilized bendamustine composition still retains the appearance of a white lyophilized powder even after being subjected to a temperature/humidity level of 40° C./75% RH for a period of 3 months. The percentage concentration of monohydroxy-bendamustine hydrochloride, after subjecting the lyophilized bendamustine composition to the stability analysis, is 0.87, while dihydroxy-bendamustine hydrochloride is not detected. The reconstitution time of the lyophilized bendamustine composition is less than 1 minute. The reconstitution time of the lyophilized bendamustine composition subjected to stability analysis for administering the lyophilized bendamustine composition to a subject is also less than 1 minute. The appearance of the reconstituted bendamustine composition is that of a solution free from visible particles of foreign matter. Furthermore, as exemplarily illustrated in FIG. 10C, the total percentage of impurities in the final bendamustine composition, after lyophilization and reconstitution, is less than 1 wt %.

Recitation of ranges of values herein are merely intended to serve as a shorthand method of referring individually to each separate value falling within a range, unless otherwise indicated herein, and each separate value is incorporated into the specification as if each separate value were individually recited herein. All methods disclosed herein can be performed in any suitable order unless otherwise indicated herein or otherwise clearly contradicted by context.

The foregoing examples have been provided merely for the purpose of explanation and are in no way to be construed as limiting of the present invention disclosed herein. The use of any and all examples or exemplary language (e.g. "such as" provided herein, is intended merely to better illuminate the present invention and does not pose a limitation on the scope of the invention unless otherwise claimed. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods, modifications, and uses, such as are within the scope of the appended claims. Moreover, any combination of the above described elements in all possible variations thereof is encompassed by the invention unless otherwise indicated herein or otherwise clearly contradicted by context. Those skilled in the art, having the benefit of the teachings of this specification, may affect numerous modifications thereto and changes may be made without departing from the scope and spirit of the invention in its aspects.

We claim:

1. A method for preparing a stable lyophilized bendamustine composition for treating a condition in a subject in need thereof, comprising:
   1) preparing a pre-lyophilization bendamustine composition consisting of bendamustine hydrochloride, an aqueous solvent selected from water, and an excipient; wherein the pre-lyophilzation bendamustine composition is prepared by the method comprising:
   mixing about 30 wt % to about 99.9 wt % by weight of an aqueous solvent with about 0.01 wt % to about 50 wt % by weight of an excipient in a first compounding vessel at a preset temperature between about −2° C. and about 15° C. until said excipient dissolves in said aqueous solvent;
   maintaining said mixed aqueous solvent and said excipient in said first compounding vessel at said preset temperature between about −2° C. and about 15° C.;
   adding about 0.01 wt % to about 90 wt % by weight of bendamustine hydrochloride to about 5 wt % of a chilled aqueous solvent in a second compounding vessel until a uniform slurry is formed;
   adding said uniform slurry to said first compounding vessel containing said mixed aqueous solvent and said excipient maintained at said preset temperature between about −2° C. and about 15° C. and mixing contents of said first compounding vessel until said contents dissolve completely;
   adjusting said contents of said first compounding vessel to a final weight using an aqueous solvent chilled at a preset temperature between about −2° C. and about 15° C.; and
   filtering said adjusted contents in said first compounding vessel through a filter membrane
   2) lyophilizing the above prepared pre-lyophilization bendamustine composition to obtain a lyophilized bendamustine composition
   3) reconstituting the lyophilized bendamustine composition with an aqueous solvent for about 30 seconds to 300 seconds, wherein the reconstituted bendamustine product contains about 0.2 wt % to about 2.5 wt % by weight of impurities and the bendamustine solution is stable for 24 hours when stored at about 2° C. to about 8° C., or stable for 3 hours when stored at room temperature, at about 15° C. to about 30° C. under room lighting.

* * * * *